US007813939B2

(12) United States Patent
Clements et al.

(10) Patent No.: US 7,813,939 B2
(45) Date of Patent: Oct. 12, 2010

(54) PHARMACEUTICAL INVENTORY AND DISPENSATION COMPUTER SYSTEM AND METHODS

(75) Inventors: Leon M. Clements, League City, TX (US); Glenn G. Hammack, Houston, TX (US); Sean C. Mitchem, Helotes, TX (US); Kelly M. Jackson, San Antonio, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 1706 days.

(21) Appl. No.: 10/806,878

(22) Filed: Mar. 23, 2004

(65) Prior Publication Data

US 2005/0216310 A1 Sep. 29, 2005

(51) Int. Cl.
*G06Q 50/00* (2006.01)
(52) U.S. Cl. .......................................... 705/2; 600/300
(58) Field of Classification Search .................. 705/2–3; 600/300
See application file for complete search history.

(56) References Cited

U.S. PATENT DOCUMENTS

| 4,857,713 | A | | 8/1989 | Brown |
|---|---|---|---|---|
| 5,291,399 | A | | 3/1994 | Chaco |
| 5,619,991 | A | | 4/1997 | Sloane |
| 5,758,095 | A | | 5/1998 | Albaum et al. |
| 5,911,132 | A | | 6/1999 | Sloane |
| 5,933,136 | A | | 8/1999 | Brown |
| 6,152,364 | A | * | 11/2000 | Schoonen et al. ............ 235/375 |
| 6,369,847 | B1 | | 4/2002 | James et al. |
| 6,587,829 | B1 | | 7/2003 | Camarda et al. |
| 6,666,820 | B1 | | 12/2003 | Poole |
| 7,129,970 | B2 | | 10/2006 | James et al. |
| 7,278,028 | B1 | * | 10/2007 | Hingoranee .................. 713/186 |
| 2002/0120471 | A1 | | 8/2002 | Drazen |
| 2003/0036683 | A1 | | 2/2003 | Kehr et al. |
| 2003/0050799 | A1 | * | 3/2003 | Jay et al. ........................ 705/2 |
| 2003/0050802 | A1 | * | 3/2003 | Jay et al. ........................ 705/3 |
| 2004/0088187 | A1 | * | 5/2004 | Chudy et al. ................... 705/2 |

(Continued)

FOREIGN PATENT DOCUMENTS

EP 0 510 615 A 10/1992

(Continued)

OTHER PUBLICATIONS

Department of Health, "A Pharmacy Service for Prisoners", Jun. 2003, Department of Health.*

(Continued)

*Primary Examiner*—Gerald J. O'Connor
*Assistant Examiner*—Sind Phongsvirajati
(74) *Attorney, Agent, or Firm*—Bracewell & Giuliani LLP

(57) ABSTRACT

A computer-implemented method and system for inventory administration and monitoring of medicines and pharmaceuticals from a pharmacy and medicinal administration facility for use in correctional facilities, such as in prisons. Information related to past medical history of a patient may be reviewed while simultaneously reviewing a prescription written for the same patient. Prescription filling tasks can also be controlled, such as printing labels for medication in batches to assist with the shipment of medication to prison units. Compliance records associated with medicinal administration of prescribed medications to patients can also be maintained.

25 Claims, 18 Drawing Sheets

U.S. PATENT DOCUMENTS

2004/0138921 A1* 7/2004 Broussard et al. .............. 705/2
2004/0193019 A1 9/2004 Wei

FOREIGN PATENT DOCUMENTS

| EP | 1 237 113 A | 9/2002 |
|---|---|---|
| WO | WO 99/41014 A | 8/1999 |
| WO | WO 2004/015602 A | 2/2004 |

OTHER PUBLICATIONS

Rainer, Ben G., MD and Stobo, John D., MD, Health Care Delivery in the Texas Prison System The Role of Academic Medicine, JAMA—The Journal of the American Medical Association; Jul. 28, 2004, pp. 485-489, vol. 292, No. 4, U.S.
Clements, et al., Presentation titled "CyberCare A Medical Delivery for the Future," Presented at The National Healthcare Congress, Miami, FL., Nov. 6, 1999.
UTMB Correctional Managed Care uses Cyb-R Care to provide remote physician services across the State of Texas, Booth Presentation, May 10, 2001.
Towards the Electronic Patient Record (TEPR), Using the Electronic Medical Record to Support Telemedicine, May 11, 2001.
Telemedicine, An Introduction, Review, and Considerations, HI 2001, May 16, 2001.
American Telemedicine Association (ATA), PowerPoint Presentation, Fort Lauderdale, Florida Jun. 5, 2001.
Business Computer Applications and the University of Texas Medical Branch Correctional Managed Care welcomes Representatives of the U.S. Federal Bureau of Prisons Washington, D.C., Aug. 14, 2001.
Digital Medical Services Telemedicine/EMR Update, VA-HHS, Aug. 15, 2001.
Digital Medical Services Telemedicine/EMR Update, ACA Philly, Aug. 23, 2001.
Digital Medical Services Technology Overview, Enron, Sep. 6, 2001.
Allen, John, UTMB Correctional Managed Care Private Prison Presentation, www.digitalmedicalservices.com, Private Prisons, Dec. 12, 2001.
Using the Emerald Reports Screens, Dec. 19, 2001.
UTMB Electronic Medical Records and Telemedicine in the Correctional Environment, www.digitalmedicalservices.com, American Correctional Association, Workshop A-2, San Antonio, Jan. 12, 2002.
Same as above—Pfizer 2002, Jan. 13, 2002.
UTMB State of the Art Telemedicine and Electronic Medical Records in the Corrections, www.digitalmedicalservices.com, American Correctional Health Services Association (ACHSA), Portland, Oregon, Mar. 16, 2002.
UTMB Digital Medical Services, Overview, Federal Bureau of Prisons Visitors, www.digitalmedicalservices.com, Mar. 27, 2002.
UTMB Digital Medical provides remote physician services across the state of Texas, Digital Medical Services (DMS) Booth 2, May 14, 2002.
Towards the Electronic Patient Record (TEPR), UTMB Correctional Managed Care Information Services, Design and Performance of the UTMB CMC Statewide EMR System, May 14, 2002.
UTMB Correctional Managed Care Uses +DMS to provide remote physician service across the state of TX, Jun. 3, 2002.
UTMB Correctional Managed Care Information Services, Future Management of EMR Implementation and Development, A Proposal to CMC Administration, Summer Quarterly Management Meeting, Open Gates, Galveston, Texas, Jul. 10, 2002.
UTMB Correctional Managed Care Information Services, The Primary Care Studio in Galveston, Texas, Administration Systems, Aug. 14, 2002.
UTMB Correctional Managed Care Information Services, Optometric Education of the Future TELEMEDICINE, American Society of Clinical Oncology (ASCO) Telemed, Oct. 4, 2002.
UTMB Correctional Managed Care Information Services, A Common Electronic Medical Record for TDCJ Unit Clinics, Tech Lubbock, Oct. 18, 2002.
UTMB Correctional Managed Care Uses +DMS to provide remote physican service across the state of TX, +DMS Booth Presentation LMC, Oct. 27, 2002.
UTMB Correctional Managed Care Uses +DMS to provide remote physican service across the state of TX www.digitalmedicalservices.com, +DMS Booth, Jan. 29, 2003.
UTMB Correctional Managed Care (CMC) Electronic Medical Record (EMR) and Digital Medical Services (DMS), Dallas County Commissioners, Mar. 26, 2003.
UTMB Correctional Managed Care Uses +DMS to provide remote physican service across the state of TX, www.digitalmedicalservices.com, +DMS Booth, Aug. 12, 2003.
UTMB Correctional Managed Care (CMC) Information Systems, Electronic Medical Record (EMR) and Digital Medical Services (DMS), www.digitalmedicalservices.com, Centers for Disease Control (CDC) Business Computer Applications (BCA), Sep. 9, 2003.
UTMB Correctional Managed Care (CMC) Information Systems, Real IP Telemedicine: A Sustained Model, www.digitalmedicalservices.com, Polycom TM, Oct. 7, 2003.
UTMB Correctional Managed Care (CMC) Information Systems, The Role of the Community Physician in the Evolving Landscape of e-Health or How We Fit Primary Care Services into an Active, Sustained Telemedicine Practice, www.digitalmedicalservices.com, Nov. 10, 2003.
UTMB Telemedicine in Managed Care, www.digitalmedicalservices.com,, Nov. 11, 2003.
Electronic Medical Records (EMR) Leadership Retreat, Texas Tech Kickoff Leadership, Huntsville, Texas, Dec. 16, 2003.
Studio Spinners, Apr. 10, 2004.
UTMB Correctional Managed Care (CMC) Information Systems, Digital Medical Systems (DMS) Cardiology, American Telemedicine Association (ATA) Cardio, Apr. 16, 2004.
UTMB Correctional Managed Care (CMC) Information Systems, Telemedicine (TM) Nuts and Bolts, Correctional Health Long Course, American Telemedicine Association (ATA) May 2, 2004.
*The University of Texas Medical Branch v. Emtel, Inc.*, Civil Action H-03-0889, Complaint for Declaratory Judgement, filed Mar. 11, 2003, United States District Court, Southern District of Texas, Houston Division.
UTMB, The University of Texas Medical Branch, Telemedicine, Digital Medical Services, and The UTMB Electronic Health Electronic Health Network presentation, Mar. 2005.
UTMB, Electronic Health Network, Remote Physician Services Telemedicine Proposal, Jul. 14, 2005.
Letter dated Sep. 13, 2002, from Emtel, Inc. to UTMB and P&O Cruise Lines, regarding U.S. Patent 6,369,847.
J. Carmenates, et al: "Impact of Automation on Pharmacist Interventions and Medication Errors in a Correctional Health Care System," Journal of the American Society of Health.
Pascal Bonnabry: "Information Technologies for the Prevention of Medication," Business Briefing: European Pharamacotherapy 2003, 'Online' 2003, pp. 1-5.
Office Action, U.S. Appl. No. 10/959,627, dated Jun. 11, 2009.

* cited by examiner

| | Unit ID | Unit Name | Facility Code | Wave | |
|---|---|---|---|---|---|
| Edit | BH | BRADSHAW | 858 | 1 | Delete |
| Edit | DB | BRISCO | 860 | 1 | Delete |
| Edit | DU | BYRD | 861 | 1 | Delete |
| Edit | CO | COFFIELD | 865 | 1 | Delete |
| Edit | CL | COLE | 866 | 1 | Delete |
| Edit | DA | DARRINGTON | 871 | 1 | Delete |
| Edit | DO | DIBOLL | 873 | 1 | Delete |
| Edit | DX | DOMINGUEZ | 874 | 1 | Delete |
| Edit | FE | FERGUSON | 883 | 1 | Delete |
| Edit | HT | HILLTOP | 896 | 1 | Delete |
| Edit | AH | HUGHES | 901 | 1 | Delete |
| Edit | HJ | HUTCHINS | 904 | 1 | Delete |
| Edit | J1 | JESTER I | 906 | 1 | Delete |

Add/Edit Prescription

Drug Name: ACETAMINOPHEN 325MG TABLET

Strength: 325MG
Route: ORAL(po)
Normal Dose: 2
Rx Date: 1/24/2007
Rx Time: 16:33
Expires:
Prior Authorization:

Refills: 0
Dose: 2
Frequency: Q4  ☑ More
Duration: 30 Days
Quantity:
Start Date: 1/24/2007
Days KOP: ☐ PRN Calculate Quantities Dispense Method: Substituion Allowed Patient Request
Special Instructions: Put your special instructions here ☐ Email Provider Version: 1.0.0.0
Last Modified: 3/19/2003 4:26:20 PM

*FIG. 12.*

Drug and Allergen Data

DRUG DRUG INTERACTIONS  There are no drug interactions.

DRUG ALLERGEN REACTIONS

| Drug Name | Allergen Name | Allergen Group | Probability |
|---|---|---|---|
| DEMADEX 10MG TABLET | LOOP DIURETICS | LOOP DIURETICS | 1 |
| DEMADEX 10MG TABLET | SWEETENERS | LOOP DIURETICS/SWEETENERS | 2 |
| M-M-R II VACCINE | INFLUENZA VIRUS VACCINES | VACCINE AND TOXOID PREPARATIONS,COMBINATIONS/INFLUENZA VIRUS VACCINES | 2 |

DUPLICATE THERAPIES

| Drug 1 Name | Drug 2 Name | Therapeutic Class |
|---|---|---|
| APAP 160MG/5ML ELIXIR | ACETAMINOPHEN 325MG TABLET | ANALGESIC/ANTIPYRETICS,NON-SALICYLATE |

| | Username: Doe, John | | Unit Receipt | | | | 1/24/2007 8:53 | |
|---|---|---|---|---|---|---|---|---|
| DOE, JANE | | | | Manifest | | | | |
| | Rx ID | Packs Sent / Packs Received | Patient | ID | SCC/NDC | Drug Name | Strength/Units Quantity | Date Sent | Ordering Unit |
| | 1462637 2 | 0 | DOE, JANE | 1069262 | 27030220209 | ERYTHROMYCIN BASE | 333MG TABS 0 | 3/24/2006 12:50:00 PM | LT-871 |
| | 1462638 2 | 0 | DOE, JANE | 1069262 | 27030780459 | ESTROGENS,CONJUGATED | 2.5MG TABS 0 | 3/24/2006 12:50:00 PM | LT-871 |
| | 1462639 2 | 0 | DOE, JANE | 1069262 | 27030780459 | ESTROGENS,CONJUGATED | 2.5MG TABS 0 | 3/24/2006 12:50:00 PM | LT-871 |
| | 1462818 2 | 0 | DOE, JANE | 598808 | 27087130806 | ZAFIRLUKAST | 20MG TABS 0 | 3/24/2006 12:50:00 PM | DA-871 |
| | 1462819 2 | 0 | DOE, JANE | 598808 | 27001260200 | ACETAMINOPHEN | 160MG/5ML BT 0 | 3/24/2006 12:50:00 PM | DA-871 |
| | 1462820 2 | 0 | DOE, JANE | 598808 | 27001260200 | ACETAMINOPHEN | 160MG/5ML BT 0 | 3/24/2006 12:50:00 PM | DA-871 |
| | 1462821 2 | 0 | DOE, JANE | 598808 | 27001260200 | ACETAMINOPHEN | 160MG/5ML BT 0 | 3/24/2006 12:50:00 PM | DA-871 |
| | 1462822 2 | 0 | DOE, JANE | 598808 | 27006450806 | AMOX TRIPOTASSIUM CLAVULANATE | 250-125MG TABS 0 | 3/24/2006 12:50:00 PM | DA-871 |
| | 1462823 2 | 0 | DOE, JANE | 598808 | 27001260200 | ACETAMINOPHEN | 160MG/5ML BT 0 | 3/24/2006 12:50:00 PM | DA-871 |
| | 1462824 2 | 0 | DOE, JANE | 598808 | 27001260200 | ACETAMINOPHEN | 160MG/5ML BT 0 | 3/24/2006 12:50:00 PM | DA-871 |
| | 1462825 2 | 0 | DOE, JANE | 598808 | 27001260200 | ACETAMINOPHEN | 160MG/5ML BT 0 | 3/24/2006 12:50:00 PM | DA-871 |
| | 1462830 2 | 0 | DOE, JANE | 598808 | 27001260200 | ACETAMINOPHEN | 160MG/5ML CONTAINERS 0 | 3/24/2006 12:50:00 PM | DA-871 |
| | 1462848 2 | 0 | DOE, JANE | 352569 | 27033480016 | FLUOXETINE HCL | 20MG CAPS 0 | 3/24/2006 12:50:00 PM | DA-871 |

PHARMACEUTICAL INVENTORY AND DISPENSATION COMPUTER SYSTEM AND METHODS

BACKGROUND OF THE INVENTION

1. Field of the Invention

The present invention relates to computer-implemented methods and systems for pharmaceutical and medicinal dispensation services and, more specifically, for pharmaceutical and medicinal dispensation services in correctional facilities.

2. Description of the Related Art

Managed healthcare is an important service that is required by law to be provided to all inmates within correctional facilities. Most correctional facilities do not have the internal resources to fully provide efficient managed healthcare services. For this reason, most correctional facilities outsource healthcare to entities that are better suited to handle healthcare on such a large scale.

Often in connection with correctional facilities, data related to inmates, such as demographic information, is maintained to provide the correctional facilities with accurate facility occupancy records and for other administrative purposes. This information has been historically maintained as a computer database on a particular computer system or network.

Correctional facilities have also maintained medical records or medical histories in a separate database on a separate computer system. The medical records have been used to record such events as provider visit results, prescription histories, lab work results, and the like. The medical records typically have been developed and maintained either by the correctional facilities or by a third party that has been providing healthcare services for the correctional facility system.

Even though the databases were created for different, specific purposes, some of the information from each of these databases would be useful in providing administrative healthcare services within the correctional facilities. However, the computer databases have been created separately in incompatible computer protocols. To effectively provide healthcare administrative services, both or more computer systems are needed. The computers need to be able to communicate with each other and provide access to the databases contained within the two separate computer systems.

In addition to the need of each computer system to be able to communicate with each other, federal regulations, such as the Health Insurance Portability and Accountability Act (HIPAA), related to confidentiality and privacy of individual health records, have created an additional feature complicating factor for those involved in dealing with medical records. Medical records are required to be kept confidential and safeguards are required to be taken to protect such records. For example, many providers have a stated policy prohibiting transfer of information related to an individual's medical record by facsimile transmission because they do not deem this to be a secure transmittal method. Security measures are required to be implemented by those providing healthcare services to limit or control access to confidential medical records.

Medicinal administrators within correctional facilities are also required to maintain records associated with the physical administration and dispensation of prescribed medication to inmates. Inmates by law must have proper medical care while in the custody of the correctional facilities. Inmates historically have filed lawsuits against the correctional facilities claiming that they have been denied proper medical care. To provide sufficient evidence that the correctional facilities has exerted its best efforts to provide proper medical care, the correctional facilities have maintained records indicating the time, type, and dosage of medication that was administered to an inmate. A guard has been present during medication administration to ensure that the inmate actually consumed the prescribed medication, unless, as in rare circumstances, the inmate was allowed to keep the medication on his or her person, which is referred to keep-on-person medication. The correctional facility has kept records indicating whether or not the inmate has actually consumed the medication. Many times the records are either paper based or kept on a standalone computer system. To maintain this information efficiently, access to the medical record and demographic databases would be helpful to assist those that provide medication administrative and dispensation services within the correctional facility.

Medication inventory within the correctional facilities has been difficult to manage effectively. The correctional facilities generally have had a central pharmacy that has been responsible for supplying medication to the individual correctional facility units within a correctional facility. The central pharmacy has had a computer system of its own that typically has not been tied into the demographic database maintained by the prison system or the medical record database maintained either by the healthcare providers or by the correctional facility. Maintaining the inventory within the prison units and the central pharmacy and shipment of the medication to the correctional facility units are additional areas that would benefit from access to the data contained within the demographic and medical record databases.

As noted above, several types of data have been required and kept separately by prison and other detention systems, such as demographic information and medical health records. To keep the contents of different databases accurate, duplicate entries were required because much of the data is the same within the different databases. The databases have been created in separate computing environments for different purposes. At present, so far as known, instances have occurred in which data has been needed from each of the separate databases. Communication between the separate databases that were created in different computer environments has not been possible because of the incompatible formats of the separate databases. Maintaining the databases has also been difficult because each prison system has its own procedure for updating its demographic and medical record databases.

SUMMARY OF THE INVENTION

The present invention advantageously provides a method for computerized monitoring of inventory of pharmaceuticals for inmates and dispensation of prescribed medication to inmates in correctional facilities. The monitoring of the inventory and dispensation of prescribed medication is performed in conjunction with computerized records including an electronic medical record stored in computer containing information about an inmate to receive the prescribed mediation and the inmate's medical history. The systems and methods of the present invention enable correctional facilities to monitor and track each dose of medication from the time that it enters the pharmacy until an inmate takes the medication.

In order to monitor the inventory of the pharmaceuticals and dispensation of the prescribed medication, the method includes reviewing the electronic medical record to verify that the prescribed medication is suitable for the inmate. The review occurs in two phases. A first phase is performed automatically by a computer upon entry of a prescription into the computer. The automatic review checks for drug—drug interacts and for known allergies. A pharmacist typically performs the second phase of the review. The pharmacist can either perform a manual review or request that the computer perform the automatic computer review again. Once the records are reviewed, authorization for release of the prescribed medication for the inmate can be performed if the prescribed medication has been verified as suitable for the inmate. A pharmacist also typically authorizes the release of the prescribed medication. Once the prescribed medication has been released, a unit packet of the prescribed medication can be labeled for dispensing to the inmate. A pharmacist technician typically performs the task of labeling individual unit packets of the prescribed medication. The unit packet of the prescribed medication can be delivered to a correctional facility unit that houses the inmate.

Upon receipt of the prescribed medication, along with other pharmaceuticals used for a floor stock at the correctional facility, the inventory of pharmaceuticals at the pharmacy from which the pharmaceuticals were sent and the inventory at the correctional facility are adjusted accordingly. Once the prescribed medication is at the correctional facility, the prescribed medication is transferred within the correctional facility unit to administer the prescribed medication to the inmate. The location from which prescribed medication is administered in correctional facilities is often called a "pill window." At the pill window, a record is formed in the computer verifying the dispensation of the unit packet of the prescribed medication to the inmate, the receipt of the prescribed medication by the inmate, and verifying whether the inmate took the unit packet of the prescribed medication. These records are used as provide verification reports to evidence that the correctional facility at least attempted to provide medical services for the inmate.

As another embodiment of the present invention, a method for computerized monitoring of inventory of pharmaceuticals for inmates in correctional facilities is advantageously provided. This monitoring of the inventory of pharmaceuticals is advantageously provided in conjunction with computer records including an electronic medical record containing information about an inmate to receive prescribed medication and the inmate's medical history. In order to monitor the inventory of pharmaceuticals, the electronic medical record is reviewed to verify that the prescribed medication is suitable for the inmate. The step of reviewing can be performed in two steps, with a first step occurring automatically upon entry of a prescription in the system. A pharmacist typically performs the second step of the review. The step of reviewing compares the prescription with the inmate's electronic medical record to ensure that there will not be a drug—drug interaction or allergic reaction. If the prescribed medication has been verified as being suitable for the inmate, the pharmacist can authorize release of the prescribed medication for the inmate.

Once the pharmacist releases the prescribed medication, a label can be printed for the prescribed medication to place upon a unit packet of the prescribed medication for dispensing to the inmate. A pharmacist technician typically controls the printing and application of labels upon the prescribed medication. The inventory of pharmaceuticals is then adjusted based upon the prescribed medication delivered to the correctional facility for dispensing to the inmate.

To improve the fault tolerance associated with the system, the methods described herein can include the step of caching each electronic medical record for each inmate contained within each wave or shipment scheduled to be shipped within a predefined time period prior to the step of reviewing the electronic medical record. The cache system used in the present invention allows the data needed to perform the reviews for a predetermined time period to be pushed to a pharmacy server where the data remains in local memory until needed. In the event that the network malfunctions, the pharmacist will be able to continue with the review for upcoming shipments without any interruptions in the system during the predetermined time period. Caching can also be used for locally storing data related to each label to be printed for each wave scheduled to be shipped within a predetermined time period prior to printing the label.

Another embodiment of the present invention advantageously includes a program storage device readable by a machine, tangibly embodying a machine readable code of program instructions executable by the machine to perform method steps of monitoring pharmaceutical inventory and monitoring dispensation of prescribed medication to inmates in correctional facilities. The monitoring pharmaceutical inventory and dispensation of prescribed medication is preferably performed in conjunction with an electronic medical record containing information about an inmate to receive the prescribed medication and the inmate's medical history. The machine readable code in the program storage device preferably include instructions for causing review of the electronic medical record, followed by authorizing release of the prescribed medication for the inmate. The machine readable code further includes instructions causing a label for the prescribed medication is then printed to place upon a unit packet of the prescribed medication, and forming a record in the computer for verifying: the dispensation of the unit packet of the prescribed medication to the inmate; the receipt of the prescribed medication by the inmate; and that the inmate took the unit packet of the prescribed medication. The records formed by the computer under control of these instructions are used to provide verification reports to evidence that the correctional facility at least attempted to provide medical services for the inmate.

As another embodiment of the present invention, a computerized system for monitoring of pharmaceutical inventory and dispensation of medication to inmates in correctional facilities in conjunction with an electronic medical record containing information about an inmate to receive prescribed medication and the inmate's medical history is advantageously provided. The system preferably includes a computer memory, and a printer for printing labels for prescribed medication. The system also preferably includes pharmacy databases, a pharmacist review workstation, a pharmacist technician workstation, a medication dispensation workstation, and a communications network.

The pharmacy databases are preferably stored in the computer memory of the pharmacy server and are preferably used for maintaining a drug formulary and a pharmaceutical inventory. The pharmacist review workstation is preferably used to enable a pharmacist to simultaneously review the inmate's electronic medical record and an inmate's prescription in the computer memory and upon review of the inmate's prescription, approve the prescription. The pharmacist technician workstation printer enables pharmacist technicians to print labels for application to the inmate's prescribed medication upon command. The medication dispensation workstation enables data entries concerning the prescribed medication to be dispensed and a medication compliance history, or medical administration record, to be recorded in the computer memory. The communications network electronically interconnects the electronic medical record database, the pharmacy databases, the pharmacist review workstation, the pharmacist technician workstation, the medication dispensation workstation, the printer, and the computer memory to enable the devices to communicate with each other.

As another embodiment of the present invention, a computerized system for monitoring pharmaceutical inventory in correctional facilities in conjunction with an electronic medical record containing information about an inmate to receive prescribed medication and the inmate's medical history is provided. The system preferably includes a computer memory and a printer. The system further includes pharmacy databases, a pharmacist review workstation, and a pharmacist technician workstation.

The pharmacy databases are preferably stored in the computer memory of a pharmacy server for maintaining records related to a drug formulary and a pharmaceuticals inventory. The pharmacist review workstation is preferably used to enable a pharmacist to simultaneously review the inmate's electronic medical record and an inmate's prescription in the computer memory and upon review of the inmate's prescription, approve the prescription. The pharmacist technician workstation is preferably used to enable pharmacist technicians to print labels with the printer for application to the inmate's prescribed medication upon command.

As yet another embodiment of the present invention, a computerized system for monitoring dispensation of medication to inmates in correctional facilities in conjunction with an electronic medical record containing information about an inmate to receive prescribed medication and the inmate's medical history. The system advantageously includes a medication dispensation workstation and a communications network.

The medication dispensation workstation is used to enable medication to be dispensed and a medication compliance history to be recorded. The medication dispensation workstation preferably includes a computer memory in a server for medical administration record, or compliance records, to be recorded. The communications network is used to enable the electronic medical record database, the pharmacy databases, the pharmacist review workstation, the pharmacist technician workstation, and the medication dispensation workstation to communicate with each other.

In all embodiments of the computerized system for monitoring dispensation of medication to inmates in correctional facilities, the system can also include pharmacy databases for maintaining records related to drug formulary and a pharmaceutical inventory.

To better understand the characteristics of the invention, the description herein is attached, as an integral part of the same, with drawings to illustrate, but not limited to that, described as follows.

BRIEF DESCRIPTION OF THE DRAWINGS

A better understanding of the present invention can be obtained when the detailed description set forth below is reviewed in conjunction with the accompanying drawings, in which:

FIG. 10 is a pictorial representation of a computer screen used to provide operators with data relating to scheduling correctional facility units to be included within shipments in accordance with an embodiment of the present invention;

FIG. 11 is a pictorial representation of a computer screen used to provide operators with data relating to inputting a prescription for a prescribed medication in accordance with an embodiment of the present invention;

FIG. 12 is a pictorial representation of a computer screen used to provide operators with data relating to adding or editing prescriptions for prescribed medication in accordance with an embodiment of the present invention;

FIG. 13 is a pictorial representation of a computer screen used to provide operators with data relating to performing a drug-drug interaction and allergy review in accordance with an embodiment of the present invention;

FIG. 14 is a pictorial representation of a computer screen used to provide operators with data relating to a medication profile of an inmate that is used to review an inmate's electronic medical record in accordance with an embodiment of the present invention;

FIG. 15 is a pictorial representation of a computer screen used to provide operators with data relating to a list of prescribed medication that has been received at a correctional facility in accordance with an embodiment of the present invention;

FIG. 16 is a pictorial representation of a computer screen used to provide operators with data relating to a medical administration record including compliance records of an inmate in accordance with an embodiment of the present invention;

FIG. 17 is a pictorial representation of a computer screen used to provide operators with data relating to indicating the prescribed medication that needs to be administered to an inmate in accordance with an embodiment of the present invention; and FIG. 18 is a pictorial representation of a computer screen used to provide operators with data relating to a list of prescriptions for inmates that need to be reviewed in accordance with an embodiment of the present invention.

Figure 1:
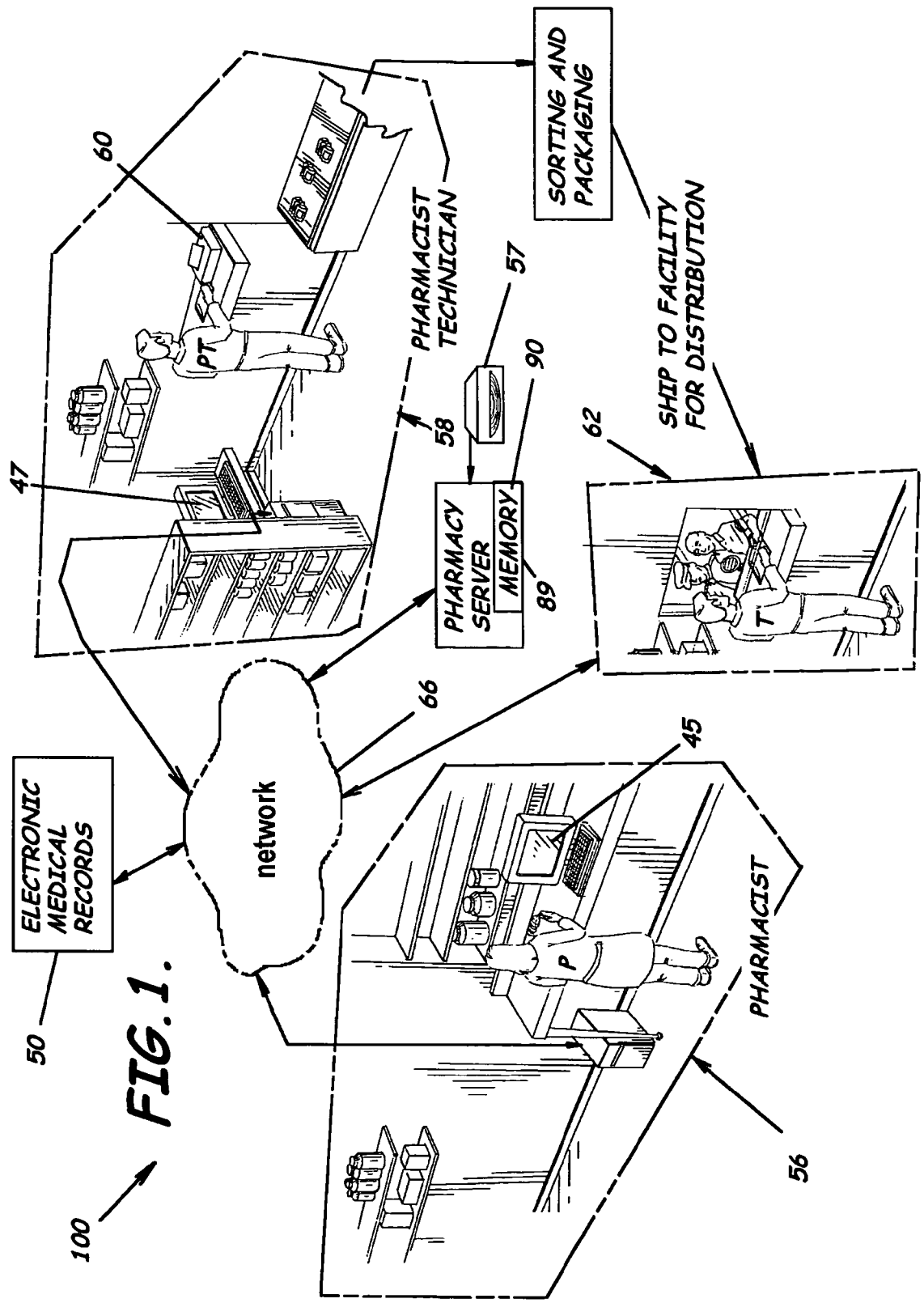
FIG. 1 is a schematic diagram of a system for computerized monitoring of inventory of pharmaceuticals for inmates and dispensation of prescribed medication to inmates in correctional facilities in accordance with an embodiment of the present invention.

To better understand the invention, we shall carry out the detailed description of some of the modalities of the same, shown in the drawings with illustrative but not limited purposes, attached to the description herein. It should be understood that where subject matter or process steps of one of the illustrated embodiments or drawing figures is of a like nature to that shown in another embodiment, like reference numerals are used for each.

DETAILED DESCRIPTION OF THE PREFERRED EMBODIMENTS

In the drawings, a high level flowchart F (FIG. 4) of a sequence of steps performed in a computer system 100 (FIG. 1) according to the present invention is shown. The present invention provides a method for computerized monitoring of inventory of pharmaceuticals for inmates or patients and dispensation of prescribed medication to inmates in correctional facilities. The computer system 100 used for providing monitoring of the inventory and dispensation of prescribed medication contains a data communication network 66, a pharmacist workstation 56, a pharmacist technician workstation 58, a medication dispensation workstation 62, a pharmacy server 89, and computerized records including an electronic medical record 50 containing information about an inmate to receive the prescribed medication and the inmate's medical history, as illustrated in FIGS. 1 and 5. The systems and methods described herein enable correctional facilities to monitor or track each prescribed medication that is prescribed to an inmate from the time that it enters the pharmacy until the prescribed medication is consumed or taken by the inmate.

Figure 4:
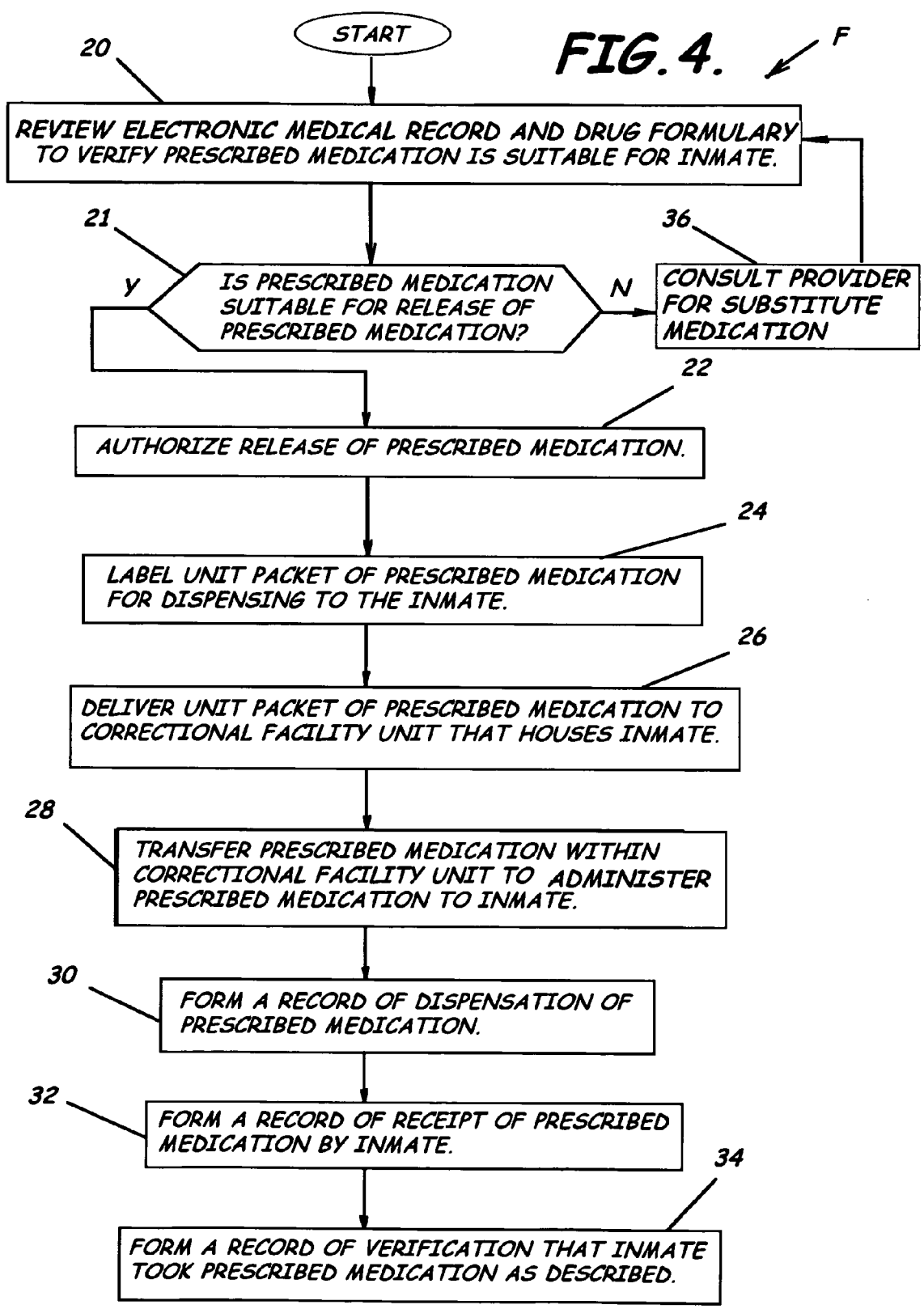
FIG. 4 is a simplified block flow diagram of the method of providing computerized monitoring of inventory of pharmaceuticals and dispensation of prescribed medication to inmates in correctional facilities in accordance with an embodiment of the present invention.
Figure 5:
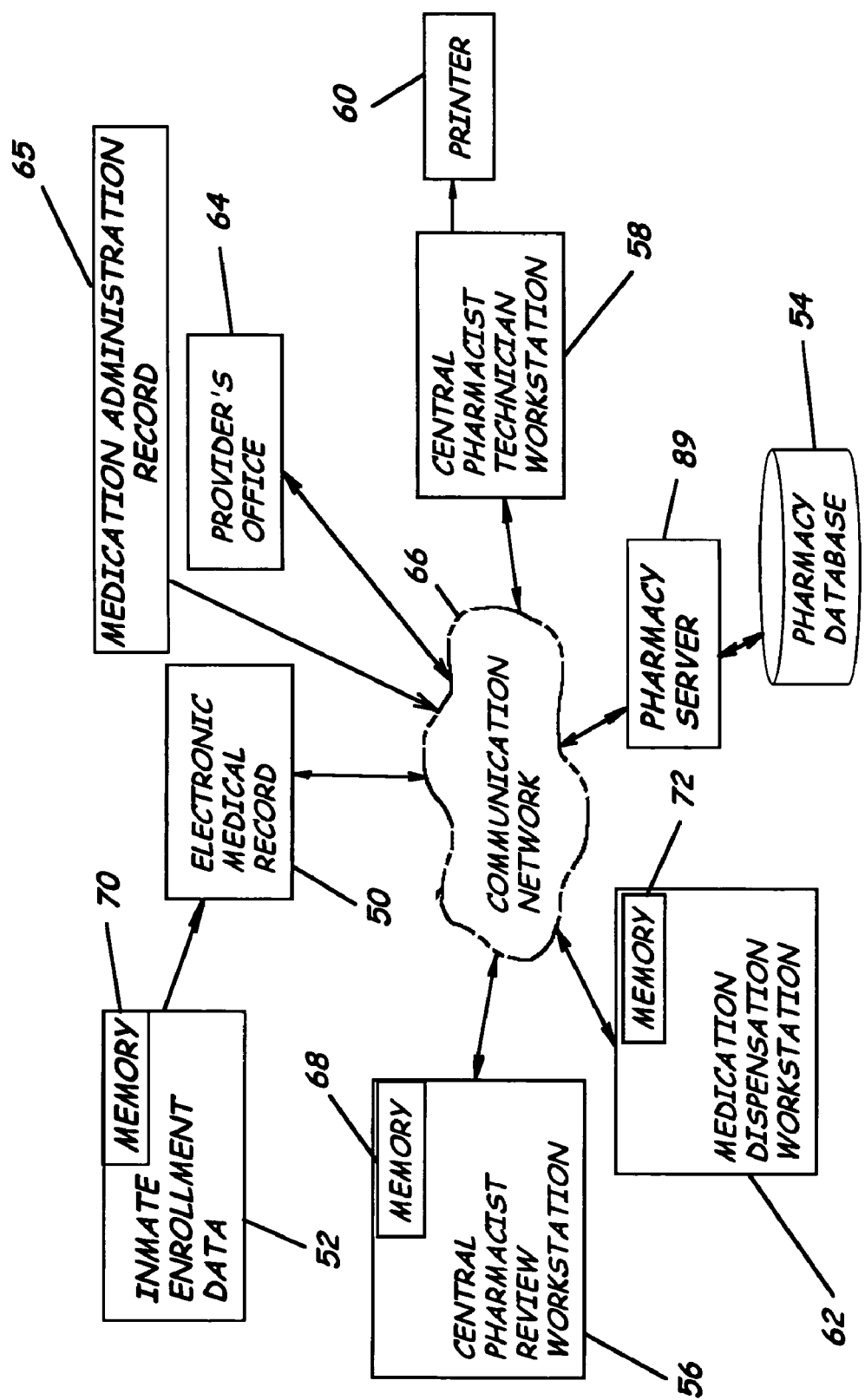
FIG. 5 is a simplified functional diagram of the components for the system for providing computerized monitoring of inventory of pharmaceuticals and dispensation of prescribed medication to inmates in correctional facilities in accordance with an embodiment of the present invention.
Figure 18:
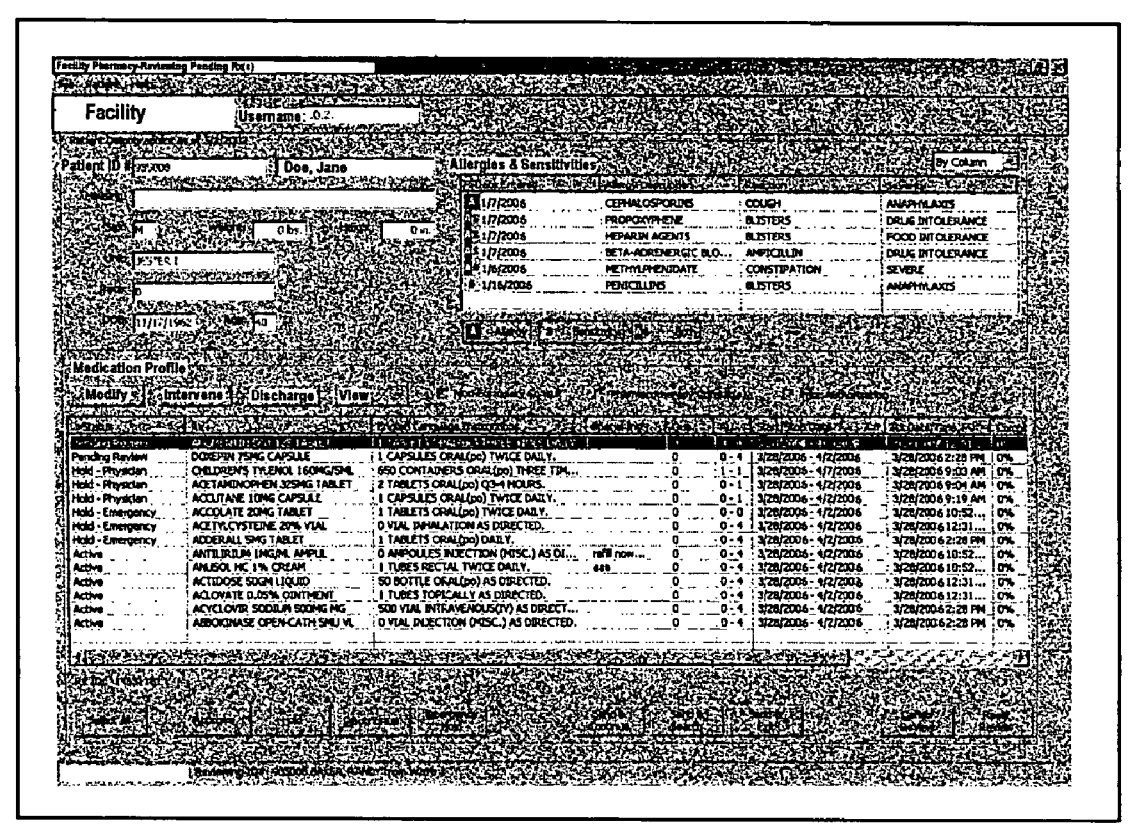

As indicated in the high-level flowchart F (FIG. 4), in order to monitor the inventory of the pharmaceuticals and dispensation of the prescribed medication, the method preferably includes reviewing the electronic medical record 50 to verify that the prescribed medication is suitable for the inmate, as indicated at step 20 in FIG. 4. The step 20 of reviewing the electronic medical record 50 includes an automatic review performed by utilizing sequences steps performed in the pharmacy server 89 under control of a computer program 57 associated with one or more servers 89, 50 upon entry of a prescription into the computerized system 100. The results of the automatic review are then forwarded over network 66 to the workstation 56 to a pharmacist P for review. During step 20 in FIG. 4, the pharmacy server 89 causes an output indication, such as those shown in FIGS. 13 and 18, on a pharmacist's display screen 45 at the workstation 56 for the pharmacist P to view. The output displayed on the pharmacist's display screen 45 lists all of the pending prescriptions for an inmate and the automatic review results, which enables the pharmacist P to complete review of prescriptions for a particular inmate before proceeding to the next inmate.

Figure 6:
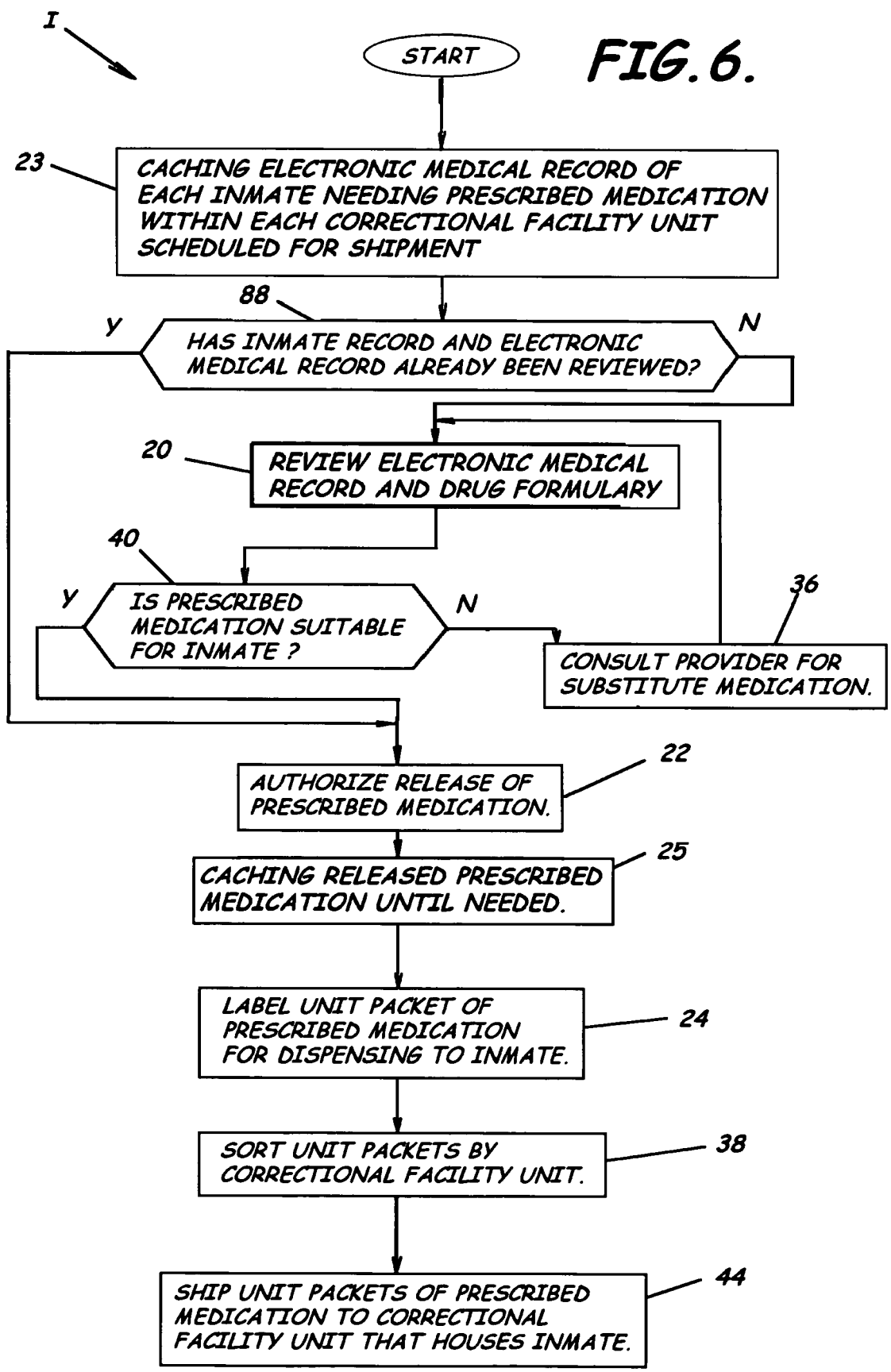
FIG. 6 is a simplified block flow diagram of the method of providing computerized monitoring of inventory of pharmaceuticals for inmates in correctional facilities in accordance with an embodiment of the present invention.

If the pharmacist P is satisfied with the automatic review results, then the pharmacist P can authorize release of the prescribed medication by utilizing a routine stored on the pharmacy server 89 as indicated in step 22 of FIGS. 4 and 6. If the pharmacist P is dissatisfied with the automatic review, the pharmacist P can request that the automatic review be performed again by utilizing a routine stored on the pharmacy server 89 or perform their own manual review prior to authorizing release of the prescribed medication. If necessary, the pharmacy server 89 can provide a prompt for pharmacist P to consult with a provider at a provider's office 64 to suggest a substitute medication, as indicated at step 36 in FIGS. 4 and 6.

Figure 11:
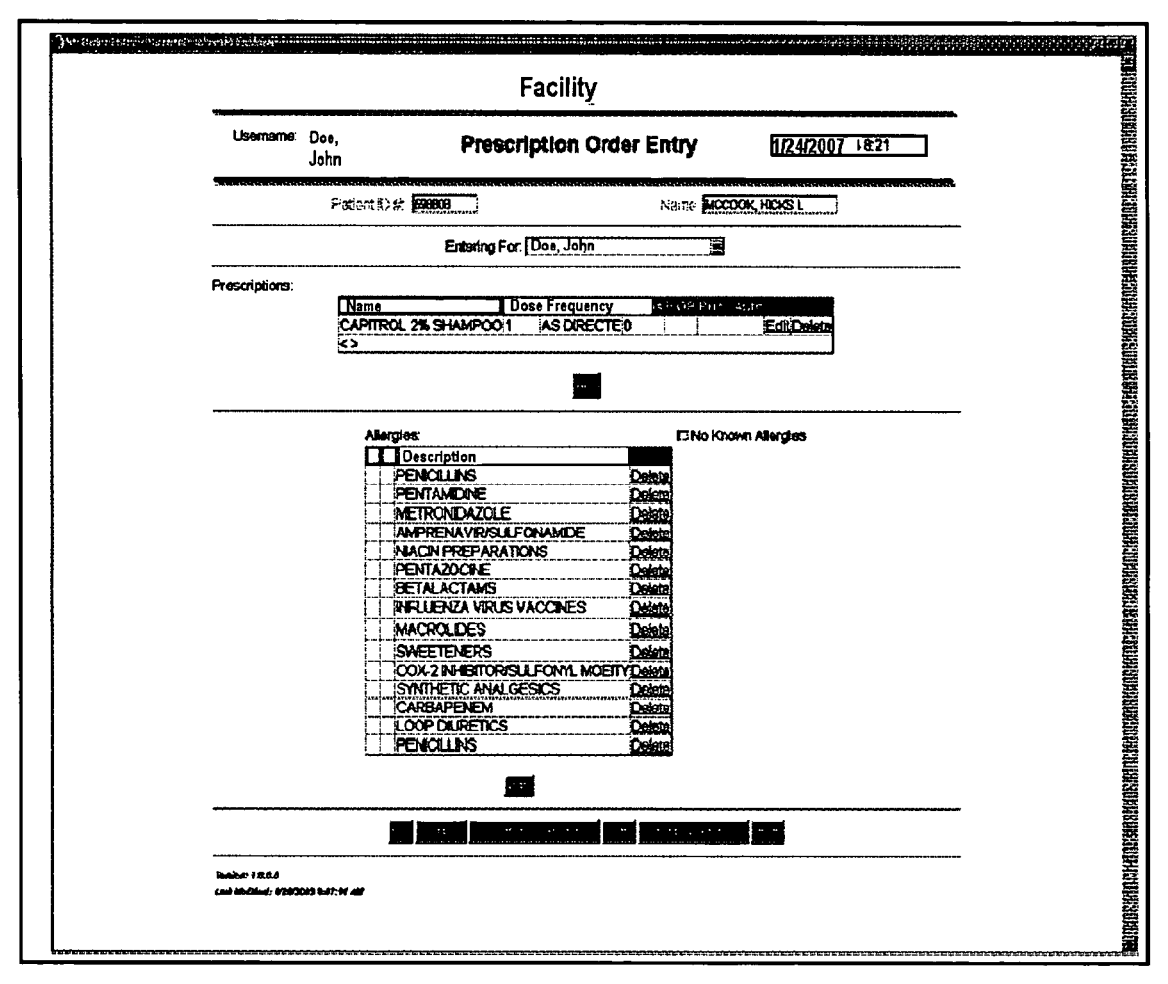

The computerized system 100 (FIG. 1) described herein can be used to enter prescriptions for inmates. A computer input screen, such as shown in FIG. 11, can be used to assist with entry of the prescription into computerized system 100. Once a prescription has been entered into the computerized system 100, the prescription can be edited by a user by accessing a routine on the pharmacy server 89. The pharmacy server 89 causes an output indication, such as shown in FIG. 12, on the pharmacist's display screen 45 that enables the user to modify the prescription, if necessary. The entry of prescriptions and modification of prescriptions can be performed by a provider or a pharmacist P, if appropriate.

Figure 14:
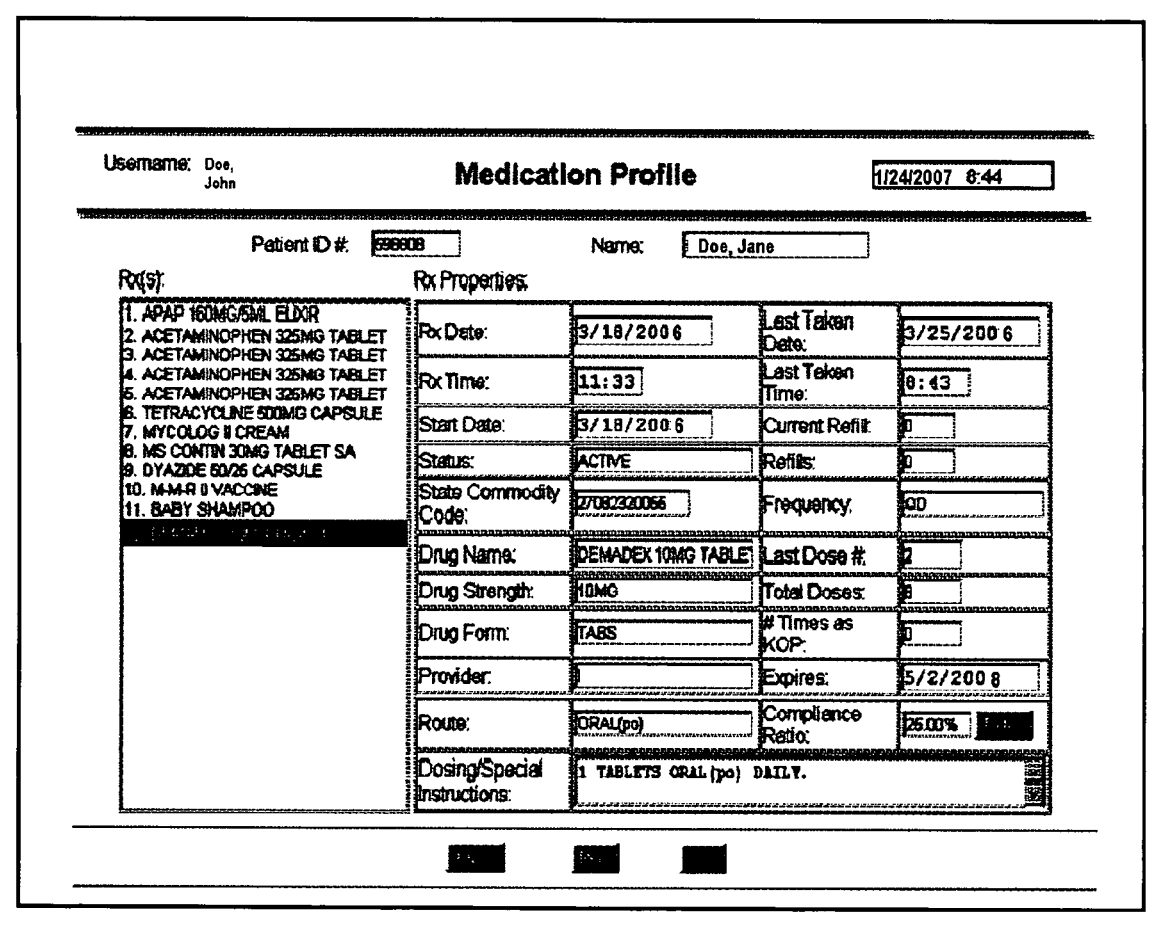

During the automatic and manual reviews, the electronic medical record 50 for the inmate is reviewed to verify that the inmate is not allergic to any medications, that there will not be a drug—drug interaction based upon all of the prescribed medication that the inmate is taking, and the like, as indicated at step 21 in FIG. 4. The results of the automatic review performed using the electronic medical record 50 can be displayed on a pharmacist's display screen 45, as shown in FIG. 13. When performing the manual review, the pharmacy server 89 causes an output indication, such as shown in FIG. 14, to be displayed on the pharmacist's display screen 45. The output indication contains all of the relevant information needed to enable the pharmacist P to review all of this information on the pharmacist's display screen 45. If all of the information related to an inmate does not fit on a single screen on the pharmacist's display screen 45, the pharmacist P has to page forward and review each page of information in order to complete the review process. Access to each inmate's entire electronic medical record 50 and requiring that each page of information be reviewed decreases the chances of the inmate being prescribed an inappropriate medication.

The electronic medical record 50 can contain various types of information related to each inmate. For example, the electronic medical record 50 can include demographic information, vital signs, lab work results, x-rays, medical checkup data, allergies, physical exam results, family history, list of current medications, drug formulary, and the like. Example demographic information about each inmate can include information such as height, weight, birth date, inmate number, and last prison unit in which the inmate has been confined. To ensure that each inmate has an electronic medical record 50, the electronic medical record 50 can be electronically interconnected so that the electronic medical record 50 is updated when new inmates are enrolled or admitted at the correctional facility, as shown in FIG. 5. For example, each evening an enrollment file or data 52 stored on a memory 70 located at a correctional facility unit can be uploaded from the correctional facility admissions computer database to the electronic medical record 50. This method of interconnecting the enrollment data with the electronic medical record 50 ensures that the electronic medical record 50 has at least a minimal amount of data related to each inmate. Alternatively, a record within the electronic medical record 50 could be created for an inmate once the inmate needs to receive medical attention. As a result of the electronic medical record 50 being updated with enrollment information, access is available to both databases within the same network 66. The electronic medical record 50 enables the correctional facilities to access data related to each inmate, regardless of which correctional facility is located.

Once the electronic medical record 50 has been reviewed, authorization for release of the prescribed medication for the inmate can be performed if the prescribed medication has been verified as suitable for the inmate, as indicated at step 22 in FIGS. 4 and 6. The pharmacist P typically authorizes release of the prescribed medication, which indicates that the prescribed medication is safe for the inmate. Once the prescribed medication has been released, a unit packet of the prescribed medication can be labeled for dispensing to the inmate, as indicated at step 24 in FIGS. 4 and 6.

Figure 3:
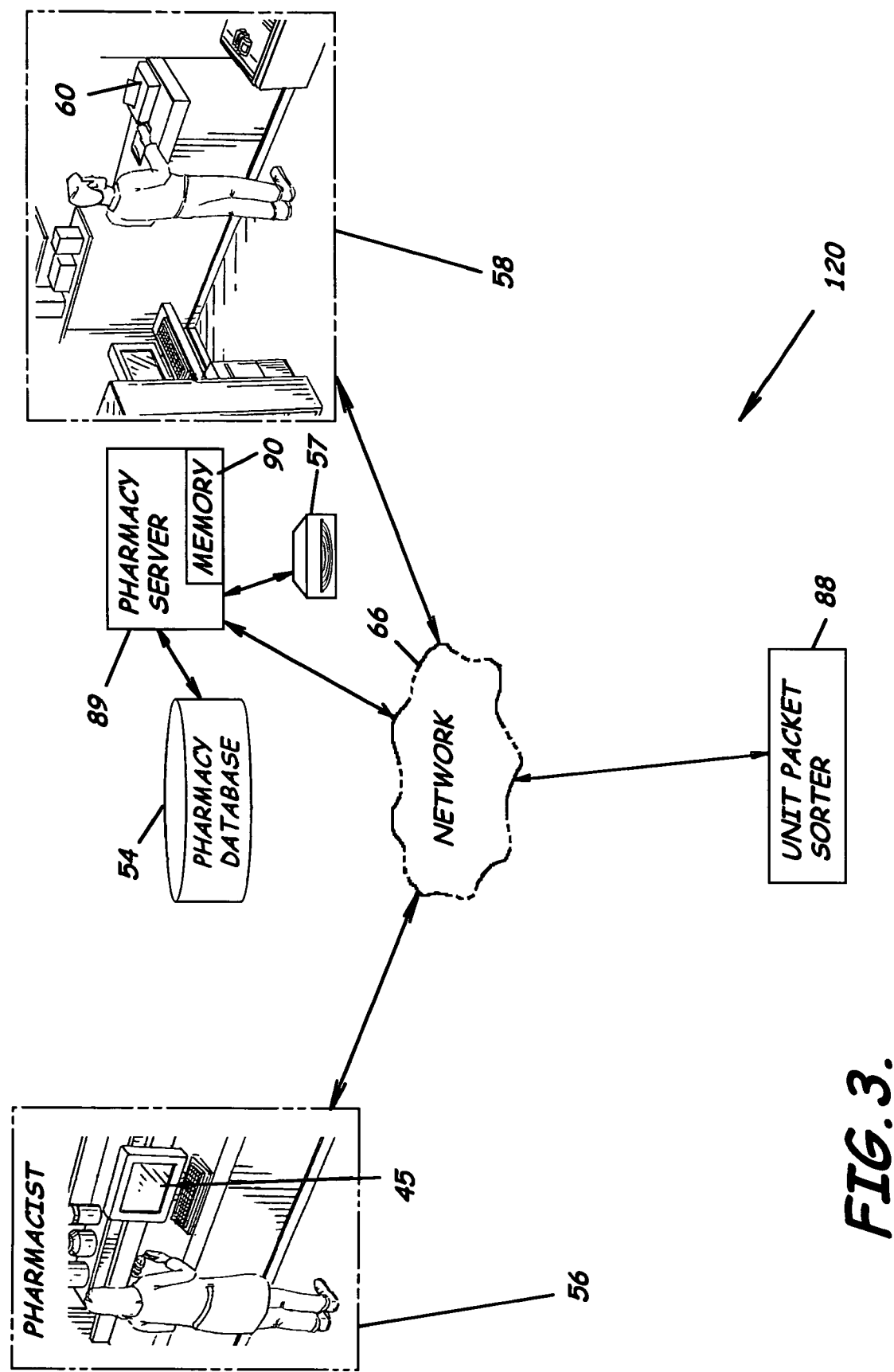
FIG. 3 is a schematic diagram of a system for computerized monitoring of inventory of pharmaceuticals for inmates in correctional facilities in accordance with an embodiment of the present invention.

As can be seen in FIGS. 1 and 3, a pharmacy technician PT at the pharmacy technician workstation 58 prints labels on printer 60 for application to the prescribed medication to label the prescribed medication. The pharmacist technician PT can control the labels that are printed to better control the workflow. For example, the pharmacist technician PT can print ten labels and then apply these ten labels to the prescribed medication.

The unit packet of the prescribed medication can be delivered to a correctional facility unit that houses the inmate, as indicated at step 26 in FIG. 4. Once the prescribed medication is at the correctional facility, the prescribed medication is transferred within the correctional facility unit to administer the prescribed medication to the inmate, as indicated at step 28 in FIGS. 4 and 7. The location from which prescribed medication is administered in correctional facilities is often called a "pill window" or medication dispensation workstation 62 that is operated by a technician T, as shown in FIGS. 5 and 6.

Figure 17:
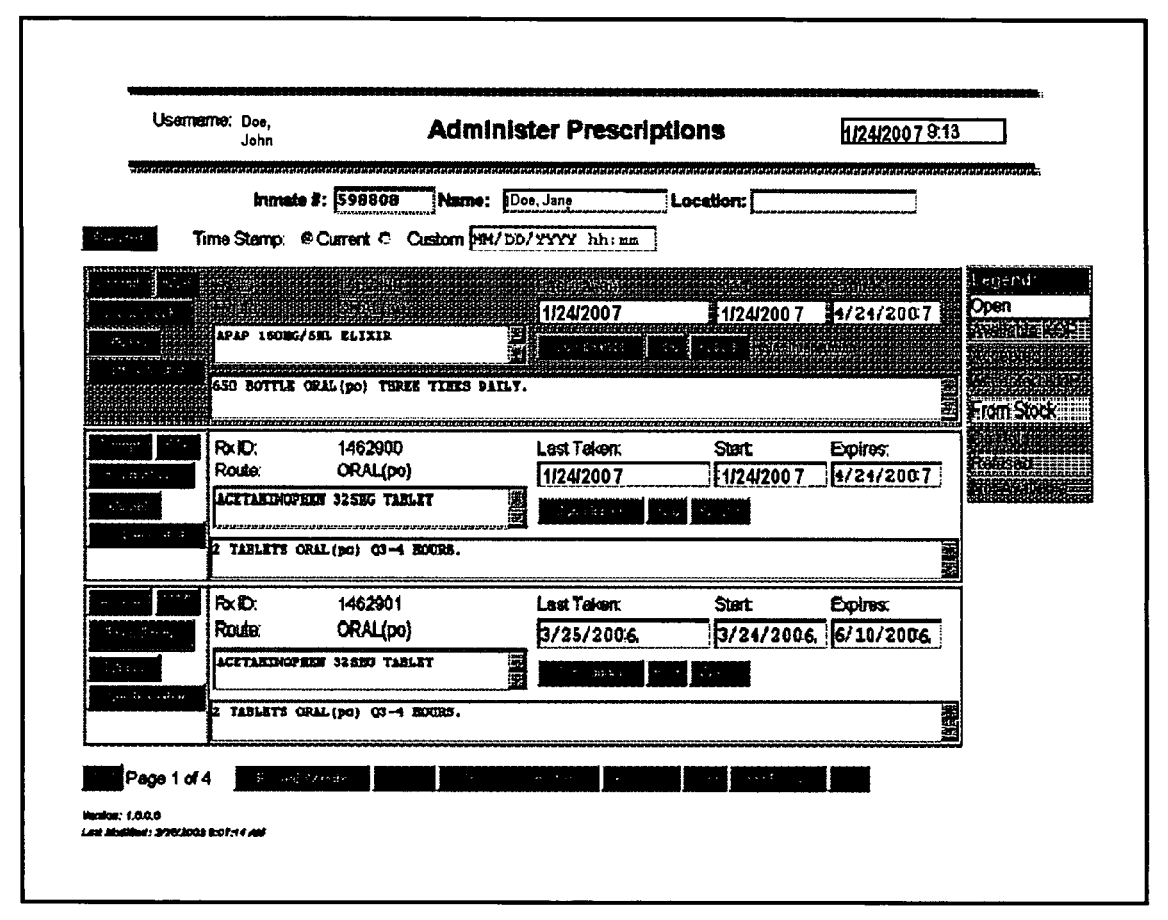

When the technician T is ready to dispense medications to an inmate, a computer screen showing all of the prescribed medications to be administered to the inmate, such as shown in FIG. 17, can be used to assist the technician T in performing their duties. At the pill window 62, the technician T physically delivers the prescribed medication to the inmate. A record is formed in the unit server 80 verifying the dispensation of the unit packet of the prescribed medication to the inmate as indicated at step 30 in FIGS. 4 and 7. Once the inmate accepts the prescribed medication, a record is formed of the receipt of the prescribed medication by the inmate as indicated at step 32 in FIGS. 4 and 7. Once the inmate takes the prescribed medication, a record is also formed verifying whether the inmate took the unit packet of the prescribed medication as indicated as step 34 in FIGS. 4 and 7. These records are used to provide verification reports to evidence that the correctional facility at least attempted to provide medical services for the inmate. In most correctional facilities, an armed guard accompanies the inmate and physically verifies that the inmate has taken the medication as prescribed.

Figure 9:
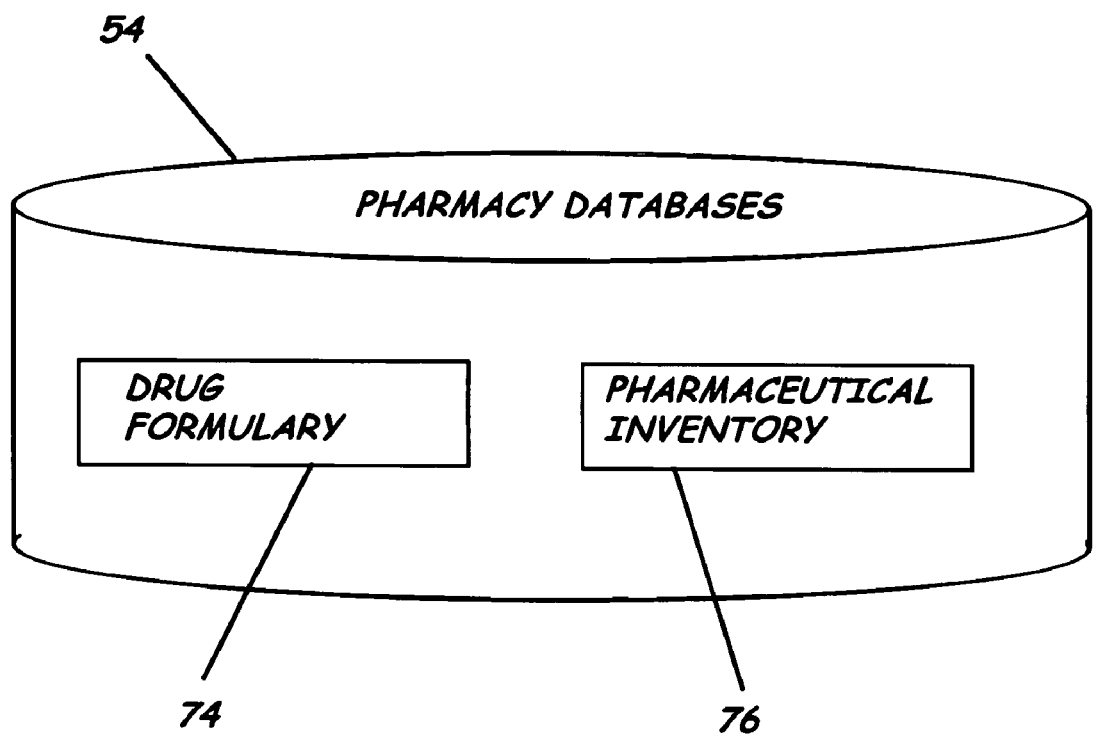
FIG. 9 is a functional diagram of pharmacy databases, including a drug formulary and a pharmaceutical inventory, in accordance with an embodiment of the present invention.

Correctional facilities typical have a drug formulary 74, which is a list of drugs that are considered to be safe and effective for patients, as well as cost effective. As shown in FIG. 9, the drug formulary 74 is one of the pharmacy databases 54 stored within pharmacy server 89. The pharmacy databases 54 can be a stand-alone databases or can be contained within or associated with the electronic medical record 50. Sometimes, more than one drug is safe and works wells in treating a disease in question. When this occurs, the less expensive drug is typically placed on the drug formulary 74 to keep costs down for the correctional facility. In order to ensure that drugs on the drug formulary 74 are used as much as possible, the method for computerized monitoring of inventory of pharmaceuticals for inmates and dispensation of prescribed medication to inmates in correctional facilities can include the step of comparing the prescribed medication with a formulary of approved medication stored in the computer upon entry of the prescription for the prescribed medication, as illustrated in FIG. 6 as indicated during step 20 in FIGS. 4 and 6. A substitute medication can be recommended if the step of comparing indicates the prescribed medication is not contained with the formulary of approved medication prior to the step of authorizing release of the prescribed medication, as indicated at step 36 in FIGS. 4 and 6.

Medication Dispensation Workstation

Figure 2:
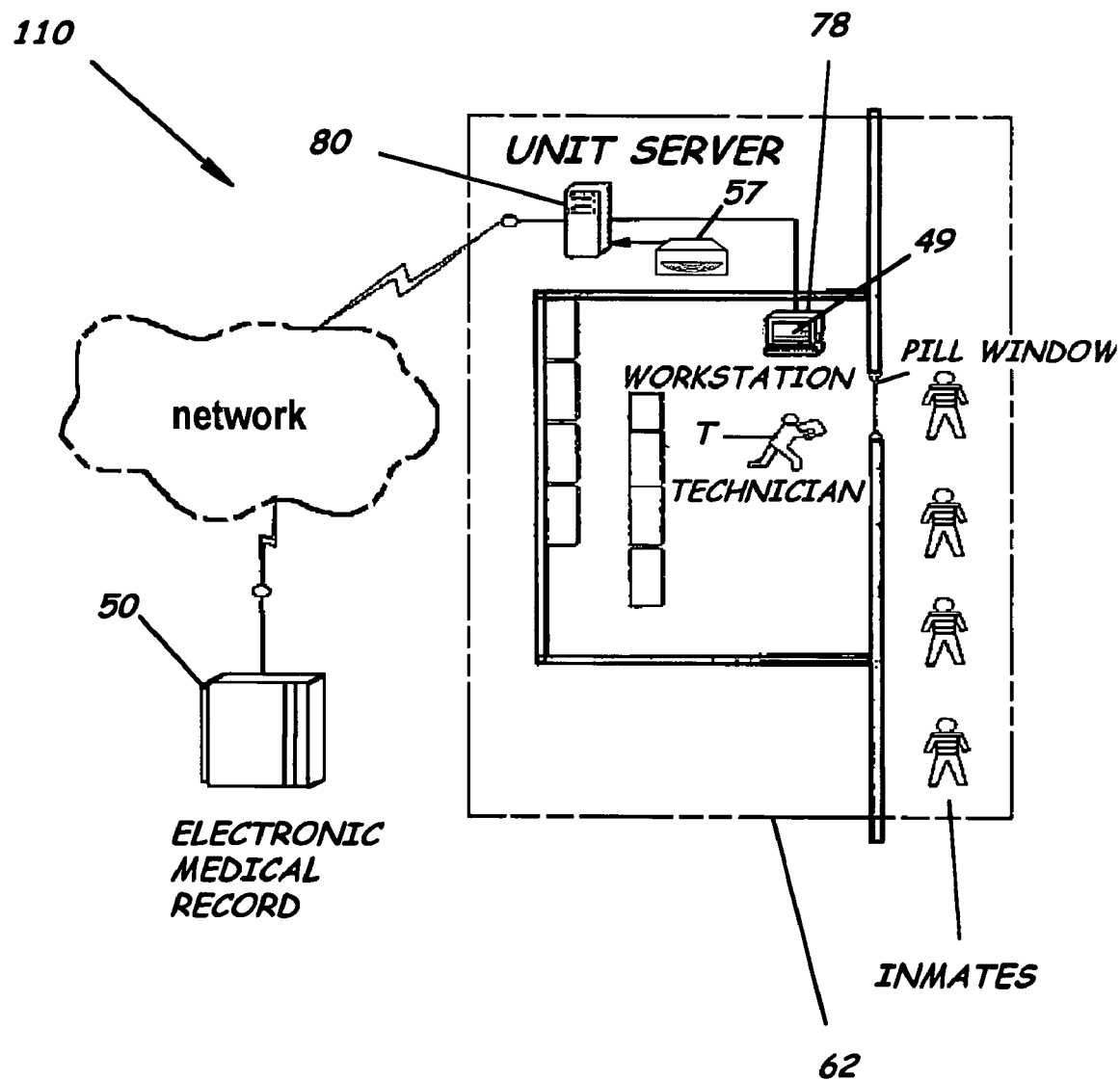
FIG. 2 is a schematic diagram of a system for computerized monitoring of dispensation of prescribed medication to inmates in correctional facilities in accordance with an embodiment of the present invention.
Figure 16:
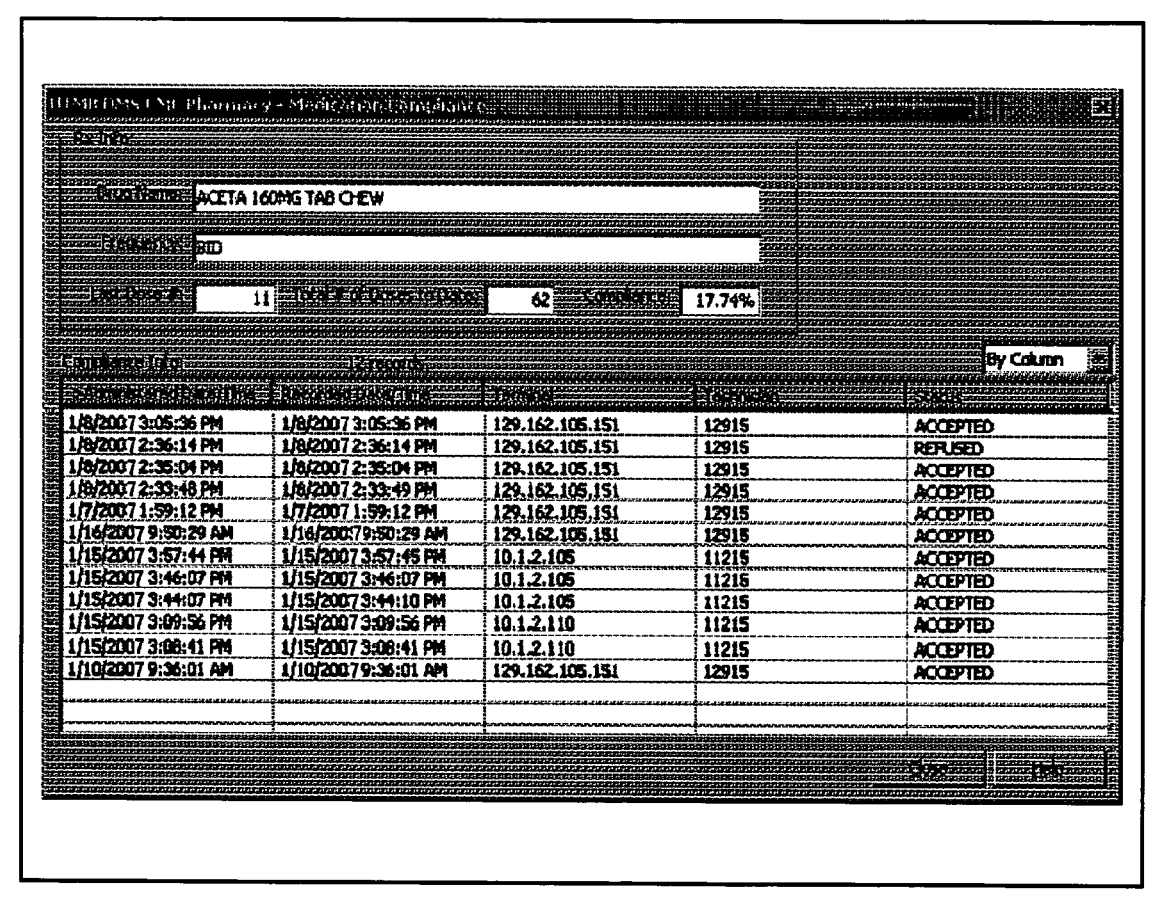

FIG. 2 illustrates in more detail the medication dispensation workstation 62, or pill window, of FIG. 1. The workstation 62 that is used to perform the method for computerized monitoring of dispensation of prescribed medication to inmates in correctional facilities. Pill windows or medication dispensation workstations 62 at correctional facilities are operated by technicians that dispense pharmaceuticals to inmates, including both prescribed medication and over-the-counter medication. The medication dispensation workstation technician or pill window technician T can review medical data related to each inmate prior to dispensation of the medication to the inmate. For example, the pill window technician T can review the inmate's electronic medical record and the medical compliance or medical administration record 65 for each patient prescription. The unit server 80 causes an output indication, such as that shown in FIG. 16, to be sent to a medication administration display screen 49, that enables the pill window technician T to view a medical compliance or medical administration record 65 for an inmate. In addition to reviewing data, the pill window technician T has the ability to record the administration of a prescription to a patient, to record administration of medication from floor stock, and to document medication errors, and to record medication waste by utilizing routines stored within the unit server 80, as indicated in steps 30, 32, 34 in FIGS. 4 and 7. At the medication dispensation workstation 62, inmates line up to receive their prescribed medication. A medication dispensation workstation 62 technician T operates the medication dispensation workstation 62. The medication dispensation workstation 62 includes a unit server 80 that operates the computer routines that enable the medication dispensation workstation 62 technician T to monitor the dispensation of prescribed medication to inmates in correctional facilities.

Figure 7:
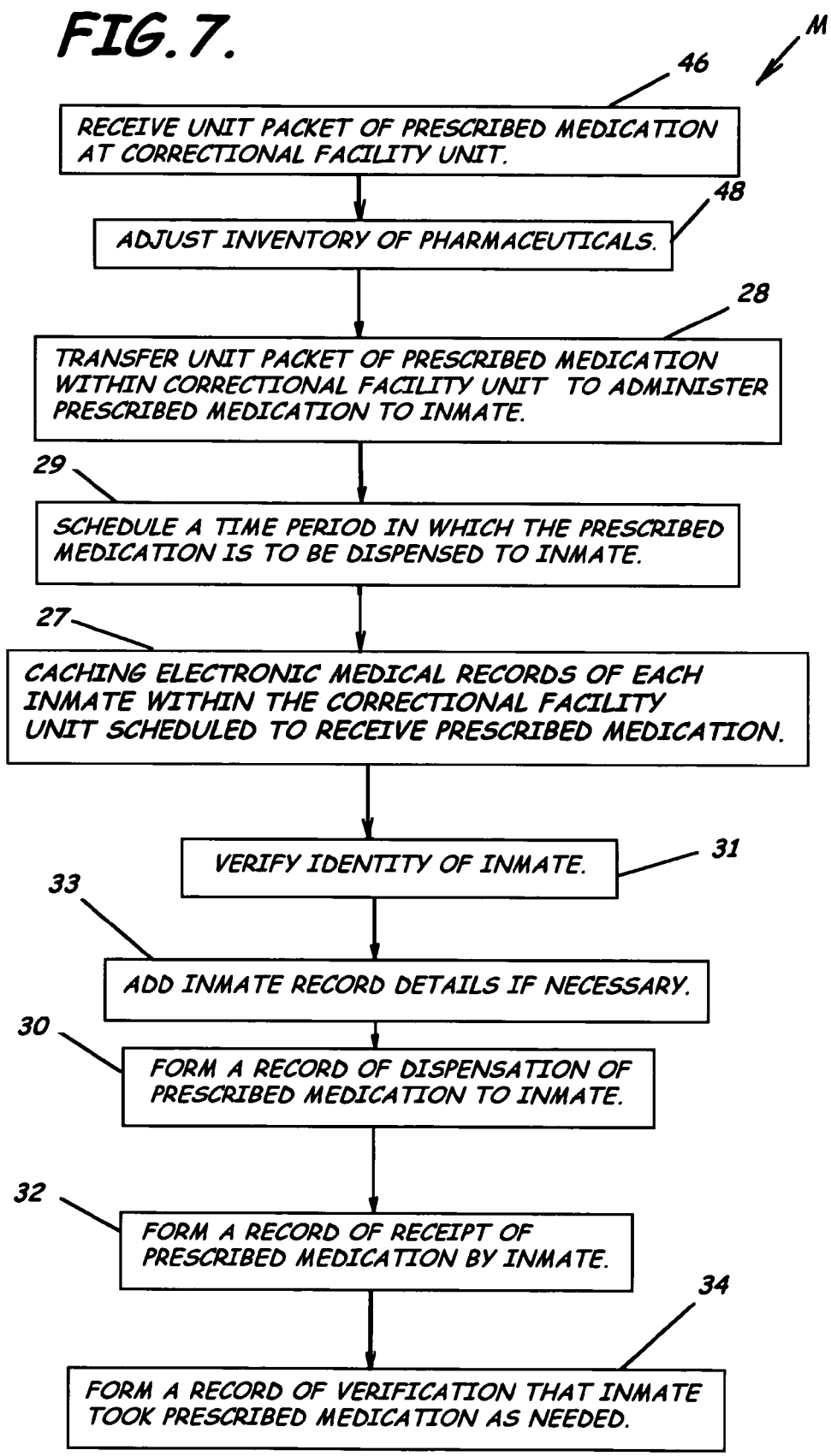
FIG. 7 is a simplified block flow diagram of the method of providing computerized monitoring of dispensation of prescribed medication to inmates in correctional facilities in accordance with an embodiment of the present invention.

The method for computerized monitoring of dispensation of prescribed medication can include the steps outlined in the high-level flowchart M shown in FIG. 7. The methods of providing computerized monitoring of dispensation of prescribed medication in correctional facilities can include receiving a unit packet of prescribed medication at the correctional facility unit, as described in step 46 in FIG. 7. Upon receipt of the unit packet of prescribed medication, the inventory of pharmaceuticals is adjusted, as described in step 48 in FIG. 7. Upon receipt of the unit packet of prescribed medication within the correctional facility, the unit packet of prescribed medication can be transferred within the correctional facility to the medication dispensation workstation 62, as described in step 28 in FIG. 7. If desired, a time period in which the prescribed medication is to be dispensed to the inmate can be scheduled in the system 110, as described in step 29 in FIG. 7.

Once the inmate is at the medication dispensation workstation 62 to receive the prescribed medication, the identity of the inmate is verified, as described in step 31 in FIG. 7. For example, in correctional facilities inmates are often provided with an identification card. A card swiper can be used to read the identification card prior to dispensing the drug to the inmate. If the owner of the identification card does not match with the person that has been prescribed the medication or the inmate at the pill window does not have an identification card, the pill window technician can refuse to dispense the prescribed medication to the inmate. Once the medication dispensation workstation technician physically distributes the prescribed medication to the inmate, a record can be formed in the unit server 80 to be uploaded to the electronic medical record 50, as indicated as step 30 of FIG. 7. A record can then be formed in the unit server 80 indicating whether or not the inmate accepted possession of the prescribed medication, as indicated at step 32 of FIG. 7. A record can also be formed indicating whether or not the inmate took or refused to take the prescribed medication, as indicated in step 34 of FIG. 7.

All embodiments of the present invention including the method for computerized monitoring of dispensation of prescribed medication to inmates in correctional facilities can include the step of adding inmate information to the computerized inmate record if information related to the inmate is not already present as indicated at step 33 in FIG. 7. For example, if an inmate develops an allergic reaction to a prescribed medication, they can inform the pill window technician T and the pill window technician can input the details surrounding the allergic reaction in the inmate's electronic medical record 50.

To enable pill window technicians to plan better, a time period in which the prescribed medication is to be dispensed to the inmate can be scheduled in the system 100, as indicated by step 29 in FIG. 7. This enables the pill window technician to determine which inmates will be present at each pill window medicine dispensation time period.

Prior to the pill window technicians forming records of dispensation, receipt, and verification that the inmate took the prescribed medication within the medication administration record 65 as indicated in steps 30, 32, 34 in FIGS. 4 and 7, inmates would file grievances against the correctional facilities claiming that the correctional facilities were not providing adequate medical care. By forming compliance records or medication administration records 65 verifying whether the inmate was administered the prescribed medication, correctional facilities can produce sufficient evidence to substantially reduce the number of claims made against them.

Figure 8:
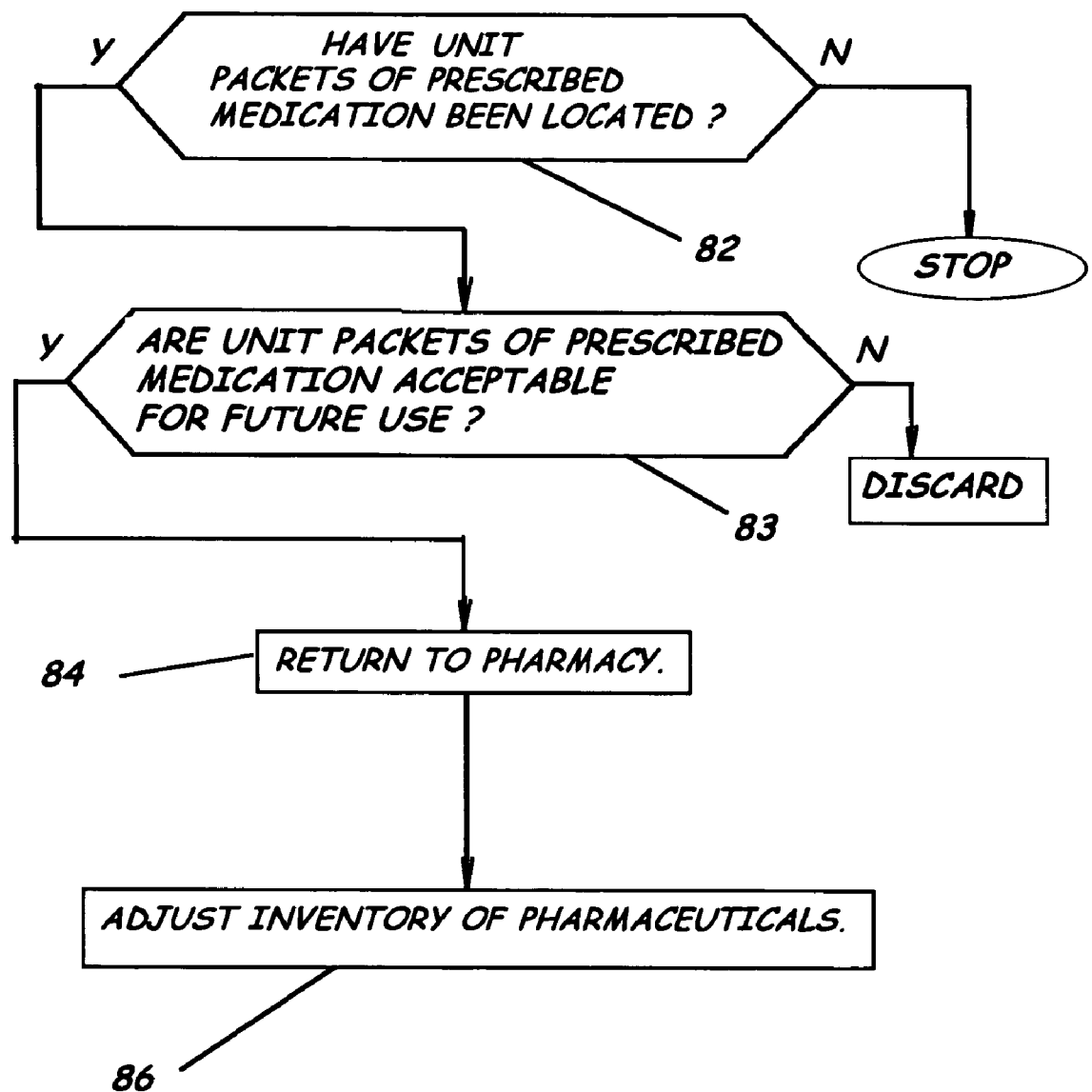
FIG. 8 is a simplified block flow diagram of the method of reclaiming prescribed medication that has been dispensed, but not taken, by inmates in correctional facilities and adjusting a pharmaceutical inventory based upon the reclamation of the prescribed medication in accordance with an embodiment of the present invention.

Some prescribed medication is not required to be taken at the pill window. These types of prescribed medication are referred to as "keep on person" medications. These "keep on person" medications are often not taken as prescribed by the inmate. Periodically, correctional facility officers go through the units and reclaim any unit packets of prescribed medication that have not been opened or disturbed as shown in FIG. 8. If there is not a compliance record of the inmate taking the unit packet of prescribed medication, the method for computerized monitoring of inventory of pharmaceuticals for inmates in correctional facilities can include the step of subsequently locating the unit packet, as indicated as step 82 in FIG. 8. If the unit packets are not suitable for future use, as indicated as step 83 in FIG. 8, then the unit packet of prescribed drugs are discarded. If the unit packets are suitable for future use as indicated as step 83 in FIG. 8, then the unit packet of prescribed medication can then be returned to a central pharmacy for reclamation, as indicated as step 84 in FIG. 8. The inventory of pharmaceuticals can be adjusted accordingly, as indicated as step 86 in FIG. 8.

As yet another embodiment of the present invention and as shown in FIG. 2, a computerized system 110, as shown in FIGS. 1 and 2, for monitoring dispensation of medication to inmates in correctional facilities in conjunction with an electronic medical record 50 containing information about an inmate to receive prescribed medication and the inmate's medical history is advantageously provided. The system 110 advantageously includes a medication dispensation workstation 62 including a unit server 80 and a communications network 66, as shown in FIG. 2.

The medication dispensation workstation 62 is used to enable medication to be dispensed and a medication compliance history or medication administration record 65 to be recorded utilizing computer routines stored on the unit server 80. The medication dispensation workstation 62 preferably includes a computer memory for medical history to be recorded. The communications network 66 is used to enable the electronic medical record 50, the pharmacy database 54, the pharmacist review workstation 56, the pharmacist technician workstation 58, and the medication dispensation workstation 62 to communicate with each other.

Central Pharmacy

As another embodiment of the present invention, a method for computerized monitoring of inventory of pharmaceuticals for inmates in correctional facilities is provided, as described in a high-level flowchart I shown in FIG. 6. The pharmacy system 120 shown in FIG. 3 is used to perform the steps required to provide computerized monitoring of inventory of pharmaceuticals for inmates in correctional facilities. The pharmacy system 120 can include a pharmacist review workstation 56, pharmacy databases 54, a pharmacy server 89, a pharmacist technician workstation 58, and a unit packet sorter 88, as shown in FIG. 3.

The monitoring of the inventory of pharmaceuticals is provided in conjunction with computer records including an electronic medical record 50 containing information about an inmate to receive prescribed medication and the inmate's medical history. In order to monitor the inventory of pharmaceuticals, the electronic medical record 50 is reviewed to verify that the prescribed medication is suitable for the inmate, as indicated as step 20 in FIG. 6. As indicated previously, the step of reviewing the electronic medical record 50 includes an automatic review performed upon entry of the prescription in the system by utilizing a computer routine stored on the server containing the electronic medical record 50 and a manual review performed by a pharmacist P. Once the prescribed medication has been verified as being suitable for the inmate, the pharmacist P can authorize release of the prescribed medication for the inmate, as described in step 22 in FIG. 6.

As a part of the pharmacist's manual review process, the system 120 described herein allows pharmacists P to review patient prescriptions after they are entered into the system 120. In addition to the prescriptions entered into the system 120, the pharmacist P can review information related to each inmate, such as a list of pending regular and refill prescriptions for the inmate, a list of medications currently on hold for the inmate, the medication profile for the inmate, the medication history for the inmate, inmate demographic and allergy information, a list of problems associated with each inmate, lab results, records related to compliance or medication administration record 65 with prior prescriptions, and clinical review data for a prescription. Pharmacists P can also view a list of missing medications that are un-reconciled for a particular correctional facility unit or specific shipment. To assist in the prescription process, the pharmacist P also has the ability to request and review prior authorization data for a prescription.

Once the pharmacist P authorizes release of the prescribed medication, a pharmacist technician PT can label the prescribed medication for the inmate. Pharmacist technicians PT can print labels for prescribed medication on printer 60 and fill patient prescriptions that have been reviewed by a pharmacist P, as shown in FIGS. 1 and 3. Pharmacist technicians PT can also reprint patient labels for prescribed medication for up to 30 days from the initial fill date.

The steps of reviewing prescriptions and printing labels for prescribed medication are performed utilizing desktop applications that are performed using the pharmacist workstation 56 and the pharmacist technician workstation 58. The pharmacist P reviewing process can consist of approving, holding, discontinuing, discharging, and re-issuing patient prescriptions. Pharmacists P can also initiate interventions and prior authorizations through the reviewing process. The printing steps are performed on printer 60, which consists of printing and re-printing labels for approved prescribed medication using pharmacist technician workstation 58.

All embodiments of the present invention including the method for computerized monitoring of inventory of pharmaceuticals for inmates in correctional facilities can include the step of sorting the unit packets in accordance with a shipping schedule for delivery of the unit packets to each correctional facility after the prescribed medication has been labeled, as indicated as step 38 of FIG. 6. The step of sorting can be accomplished with a unit packet sorter 88, as indicated as step 38 of FIG. 6. Unit packet sorter 88 can be a sorter that is capable of sorting the unit packets into waves. A suitable sorter is manufactured by Accusort. Other suitable sorters will be known to those of ordinary skill in the art and are to be considered within the scope of the present invention.

Delivery of prescribed medication to correctional facility units are made in accordance with a shipping schedule. The units that are included in each shipment can be configured using the methods and systems described herein. A computer screen that enables users to schedule which correctional unit to be included within each shipment can be used, such as shown in FIG. 10.

All embodiments of the present invention including the method for computerized monitoring of inventory of pharmaceuticals for inmates in correctional facilities can include the step of updating the inventory of pharmaceuticals at the correctional facility in response to the step of delivering the unit packet of the prescribed medication to a correctional facility unit, as indicated as step 48 in FIG. 7.

Once a prescription for prescribed medication has been deemed acceptable by a pharmacist P for a particular inmate, the prescription can be refilled automatically without the need to review the electronic medical record 50 again, as indicated as step 88 in FIG. 6. Authorization to release the prescribed medication is automatically made by the computer without the need of intervention by the pharmacist P. Automatic refilling of prescribed medication enables the correctional facilities to better utilize its limited resources and prevent duplicative work from being performed.

To ensure that the prescribed medication is ready for delivery to the facility unit, the methods described herein can also include sorting the unit packets in accordance with a shipping schedule for delivery of the unit packets to each correctional facility, as indicated as step 38 in FIG. 6, after the prescribed medication has been labeled. The step of sorting can be accomplished with a unit packet sorter 88. The pharmacy server 89 can cause an output indication on pharmacy technician workstation display screen 47 for the pharmacy technician PT to be able to select which correctional facilities are to be included within each shipment, as shown in FIG. 10. These features enable the pharmacist P and pharmacy technician PT to ensure that all of the unit packets of prescribed medication that are supposed to be sent to a facility unit are ready for shipment.

When the unit packets are shipped to a correctional facility unit, a manifest is included with the unit packets to verify what prescribed medication was shipped to a facility unit. The methods of monitoring pharmaceutical invention can include the step of updating the inventory of pharmaceuticals at the correctional facility, as indicated as step 48 in FIG. 7, in response to the step of delivering the unit packet of the prescribed medication to a correctional facility unit, as indicated as step 46 in FIG. 7. The unit server 80 causes an output indication on medication dispensation workstation display screen 49, such as shown in FIG. 15, for a user to input the list of prescribed medications into the system 100, thereby updating the pharmaceutical inventory. To input the list, the manifest can be scanned into the system 100.

To improve the fault tolerance associated with the system, the methods described herein can include the step of caching each electronic medical record 50 for each inmate for each prescribed medication scheduled to be shipped within a predefined time period prior to the step of reviewing the electronic medical record 50 as indicted in step 23 in FIG. 6. The cache system used in the present invention allows the data needed to perform the reviews for a predetermined time period to be pushed to a pharmacy server 89 where the data remains in local memory until needed. In the event that the network 66 malfunctions, the pharmacist P will be able to continue with their reviews for upcoming shipments without any interruptions in the computerized 100 during the predetermined time period. Caching can also be used for locally storing data related to each label to be printed for each wave scheduled to be shipped within a predetermined time period prior to printing the labels on printer 60, as indicated in step 25 in FIG. 6.

To assist in the methods of monitoring the pharmaceutical inventory, prescribed medication can also be reclaimed using the methods and systems described herein. If no record is received of the inmate taking the unit packet of prescribed medication, the prescribed medication can be reclaimed. As described in FIG. 8, the methods described herein can include subsequently locating the unit packet in an unbroken or suitable for use state, as indicated at step 82 in FIG. 8. If the unit packet of prescribed medication is in an acceptable form, as indicated at step 83 in FIG. 8, the unit packet of prescribed medication can be returned to a central pharmacy for reclamation, as indicated at step 84 in FIG. 8. Once the drugs are returned to the pharmacy, the inventory of pharmaceuticals can be adjusted accordingly, as indicated at step 86 in FIG. 8.

According to the present invention, a computer program product 57, associated with one or more services, operating under the sequence of instructions described below causes steps to be performed to monitor pharmaceutical inventory and monitor dispensation of prescribed medication to inmates in correctional facilities. The present invention advantageously includes a program storage device D readable by a machine, tangibly embodying a machine-readable code of program instructions executable by the machine to perform method steps of monitoring pharmaceutical inventory and monitoring of dispensation of prescribed medication to inmates in correctional facilities. The monitoring pharmaceutical inventory and dispensation of prescribed medication is preferably performed in conjunction with the electronic medical record 50 containing information about an inmate to receive prescribed medication and the inmate's medical history. The method steps of the program instructions in the machine-readable code in the program storage device preferably include reviewing the computerized inmate record and the electronic medical record 50. Release of the prescribed medication for the inmate is then authorized following review of the inmate record and the inmate's electronic medical record 50. A label for the prescribed medication is then printed on printer 60 to place upon a unit packet of the prescribed medication. A record is then formed in the computer verifying the dispensation of the unit packet of the prescribed medication to the inmate, the receipt of the prescribed medication by the inmate, and verifying whether the inmate took the unit packet of the prescribed medication. These records are used to provide verification reports to evidence that the correctional facility at least attempted to provide medical services for the inmate.

As another feature of the present invention, a computerized system S for monitoring of pharmaceutical inventory and dispensation of medication to inmates in correctional facilities in conjunction with an electronic medical record 50 containing information about an inmate to receive prescribed medication and the inmate's medical history is advantageously provided. The system 100 preferably includes a computer memory, and a printer 60 for printing labels for prescribed medication. The system 100 also preferably includes a pharmacy database 54, a pharmacist review workstation 56, a pharmacist technician workstation 58, a medication dispensation workstation 62, and a communications network 66.

The pharmacy databases 54 are preferably stored in the pharmacy server 89 and is preferably used for storing records related to an inmate's pharmaceutical history and for storing information related to formulary medications. The pharmacist review workstation 56 is preferably used to enable a pharmacist P to simultaneously review the inmate's electronic medical record 50 and an inmate's prescription in the computer memory and upon review of the inmate's prescription, approve the prescription. The pharmacist technician workstation 58 printer 60 enables pharmacist technicians to print labels with the printer 60 for application to the inmate's prescribed medication upon command. The medication dispensation workstation 62 enables the prescribed medication to be dispensed and a medication compliance history or medication administration record 65 to be recorded in the unit server 80. The communications network 66 electronically interconnects the electronic medical record 50, the pharmacy databases 54, the pharmacist review workstation 56, the pharmacist technician workstation 58, the medication dispensation workstation 62, the printer 60, and the computer memory to enable the devices to communicate with each other.

As a further aspect of the present invention and as shown in FIG. 3, a computerized system 110 for monitoring pharmaceutical inventory in correctional facilities in conjunction with an electronic medical record 50 containing information about an inmate to receive prescribed medication and the inmate's medical history is advantageously provided. The system 120 preferably includes a computer memory 91 and a printer 60. The system 120 further includes pharmacy databases 54, a pharmacy server 89, a pharmacist review workstation 56, and a pharmacist technician workstation 58, as illustrated in FIGS. 1 and 3.

The pharmacy database 54 is preferably stored in the computer memory of the pharmacy server 89 for maintaining records related to a drug formulary 74 and a pharmaceutical inventory 76, as shown in FIG. 9. The pharmacist review workstation 56 is preferably used to enable a pharmacist P to simultaneously review the inmate's electronic medical record 50 and an inmate's prescription in the computer memory of the pharmacy server 80 and upon review of the inmate's prescription, approve the prescription. The pharmacist technician workstation 58 is preferably used to enable pharmacist technicians PT to print labels with the printer 60 for application to the inmate's prescribed medication upon command.

In all embodiments of the computerized system for monitoring pharmaceutical inventories for inmates in correctional facilities, the system 110 can also include pharmacy databases 54, including a drug formulary 74 and a pharmaceutical inventory 76, as shown in FIG. 9.

As used herein, the term correctional facility can be any type of confinement facility, such as state and federal prisons or youth correctional facilities. Examples of correctional facilities include the Texas Youth Commission and the Federal Bureau of Prisons. It is envisioned that the present invention can also be used in other types of facilities, such as nursing homes, that require both medicinal administration and a tracking mechanism to document whether or not patients have been taking their medicine and as evidence to show that the facility has at least attempted to render proper medical care to the patient.

As used herein, the term prescribed medication can be a medication that is prescribed by a provider. The prescribed medication can be either a medication requiring a prescription from a doctor or an over-the-counter medication prescribed by a provider.

The invention has been sufficiently described so that a person with average knowledge in the matter may reproduce and obtain the results mentioned in the invention herein. Nonetheless, any skilled person in the field of technique, subject of the invention herein, may carry out modifications not described in the request herein, to apply these modifications to a determined structure, or in the manufacturing process of the same, requires the claimed matter in the following claims; such structures shall be covered within the scope of the invention.

It should be noted and understood that there can be improvements and modifications made of the present invention described in detail above without departing from the spirit or scope of the invention as set forth in the accompanying claims.

What is claimed is:

1. A method for computerized monitoring of dispensation of pharmaceuticals to inmates and dispensation of prescribed medication to prisoners within correctional facilities defining inmates in conjunction with computerized records including an electronic medical record containing information about a specific inmate to receive prescribed medication and the inmate's medical history, the method comprising the steps of:

reviewing the inmate's electronic medical record to verify that the prescribed medication is suitable for the inmate responsive to electronic medical record data contained therein, the electronic medical record stored in computer memory of a first computer defining a computerized records computer configured to manipulate and store the computerized records including the electronic medical record;

authorizing release of the inmate's prescribed medication by a pharmacist located at a central pharmacy responsive to the prescribed medication being verified as suitable for the inmate;

labeling a unit packet of the inmate's prescribed medication for dispensing to the inmate responsive to the authorization;

delivering the unit packet of the inmate's prescribed medication to a correctional facility unit that houses the inmate, the correctional facility unit located remote from the central pharmacy;

transferring the unit packet of the inmate's prescribed medication within the correctional facility unit to administer the inmate's prescribed medication to the inmate;

performing an automated verification that the inmate is the inmate who has been prescribed the inmate's prescribed medication by a second computer defining a correctional facility unit computer prior to forming a record of dispensing the unit packet of the inmate's prescribed medication to the inmate responsive to the inmate swiping an identification card through a card swiper, the correctional facility unit computer configured to store computerized dispensation, received verification, and administration records, dispensing the unit packet of the inmate's prescribed medication to the inmate;

forming a record of dispensing the unit packet of the inmate's prescribed medication to the inmate in computer memory of the correctional facility unit computer responsive to the dispensing of the prescribed medication to the inmate, the correctional facility unit computer positioned in communication with the computerized records computer to update the inmate's electronic medical record;

verifying receipt by the inmate of the unit packet of the inmate's prescribed medication;

forming a receipt verification record in the computer memory of the correctional facility unit computer indicating verification that the inmate received the unit packet of the inmate's prescribed medication responsive to the verification of receipt by the inmate;

performing an actual physical verification verifying whether or not the inmate consumed the inmate's prescribed medication;

performing one of the following administration verification steps:
   forming an administration verification record in the computer memory of the correctional facility unit computer indicating an actual physical verification that the inmate consumed the inmate's prescribed medication responsive to the verification of consumption by the inmate, and
   forming the administration verification record in the computer memory of the correctional facility unit computer indicating that the inmate did not consume the unit packet of the inmate's prescribed medication when so occurring;

updating the inmate's electronic medical record by the computerized records computer responsive to receiving the administration verification record from the correctional facility unit computer;

receiving a data entry from a correctional facility pill window technician for the respective correctional facility unit indicating an allergic reaction to the inmate's prescribed medication; and updating the inmate's electronic medical record over a communications network responsive to the step of receiving the data entry indicating an allergic reaction to the inmate's prescribed medication.

2. The method of claim 1,
wherein the inmate's electronic medical record includes laboratory results, medical checkup data, and problems associated with the inmate; and
wherein the step of reviewing the inmate's electronic medical record includes performing the step of automatically reviewing the electronic medical record for drug-drug interactions, duplicate therapies, and allergies by a third computer defining a pharmacy computer responsive to entry of a prescription for the inmate in the computer memory of one or more of the following: the computerized records computer and the pharmacy computer.

3. The method of claim 2, wherein the step of reviewing the inmate's electronic medical record further includes performing the step of manually reviewing a substantial portion of the inmate's electronic medical record to include the laboratory results, medical checkup data, and problems associated with the inmate contained within the electronic medical record prior to the pharmacist authorizing release of the prescribed medication to thereby reduce risk of assignment of an inappropriate medication.

4. The method of claim 2, further comprising the step of performing an automated comparison of the inmate's prescribed medication with a drug formulary of approved medication approved by the specific correctional facility unit housing the inmate responsive to computer system entry of a prescription into the computer memory of one or more of the following: the computerized records computer and the pharmacy computer.

5. The method of claim 1, further comprising the step of preventing a potential disruption of medication administration resulting from a breakdown in network communications between the computerized records computer and the correctional facility unit computer located remotely therefrom by caching on the correctional facility unit computer at least portions of each electronic medical record for each inmate scheduled to receive prescribed medicines.

6. The method of claim 1, further comprising the step of:
   adding inmate enrollment data records to the inmate's electronic medical record when information related to a new inmate is not already present, the enrollment data being uploaded from a correctional facility admissions computer located at the correctional facility unit to the inmate's electronic medical record over a communications network.

7. The method of claim 1, further comprising the step of:
   sorting each of a plurality of unit packets for each separate one of a plurality of inmates into a shipment in accordance with a shipping schedule for delivery of the unit packets to the correctional facility unit after each of the plurality of unit packets of prescribed medication including the inmate's prescribed medication has been labeled and prepared for shipment.

8. The method of claim 7,
wherein the plurality of unit packets for each separate one of the plurality of inmates comprises a 30 day supply of unit packets for each of a plurality of different prescribed medications for each separate one of the plurality of inmates; and
wherein the method further comprises the step of performing an automated update of an inventory record of pharmaceuticals at the correctional facility unit in response to receiving the shipment, the shipment received from a facility affiliated with the central pharmacy.

9. The method of claim 7,
wherein the plurality of unit packets for each separate one of the plurality of inmates comprises a 30 day supply of unit packets for a plurality of different prescribed medications for each separate one of the plurality of inmates; and
wherein the method further comprises performing the following steps responsive to the failure of an inmate to consume at least one unit packet of the inmate's prescribed medication:
   subsequently locating the at least one unit packet of the inmate's prescribed medication,
   returning the at least one unit packet of the inmate's prescribed medication, when determined to be suitable for future use, to a central pharmacy for reclamation, and
   adjusting the inventory of pharmaceuticals accordingly.

10. The method of claim 9, further comprising the step of:
   performing an automated adjustment of an inventory record of pharmaceuticals for each inmate responsive to the step of delivering one or more unit packets of the inmate's prescribed medication to the correctional facility unit that houses the respective inmate.

11. The method of claim 1, further comprising the step of: preventing a potential disruption of medication delivery resulting from a breakdown in network communications between the computerized records computer storing inmate electronic medical records and a remote pharmacy computer located remotely therefrom by caching on the remote pharmacy computer each electronic medical record for each inmate contained within each shipment scheduled to be shipped within a predefined time period prior to the step of reviewing the inmate's electronic medical record.

12. The method of claim 1, further comprising the step of: preventing a potential disruption of medication delivery resulting from a breakdown in network communications between the computerized records computer storing inmate electronic medical records and a remote pharmacy computer located remotely therefrom by caching data related to each label to be printed for each of a plurality of shipments to a corresponding plurality of correctional facilities scheduled to be shipped within a predefined time period prior to printing the respective label.

13. The method of claim 1, further comprising the step of: automatically refilling the prescribed medication for chronic conditions once the step of reviewing a computerized inmate correctional facility record and the step of reviewing the inmate's electronic medical record to verify that the prescribed medication is suitable for the inmate, has been performed for the inmate's prescribed medication.

14. The method of claim 1, further comprising the steps of: scheduling a time period that the correctional facility unit in which each inmate's prescribed medication of a plurality of inmates in the correctional facility unit is to be dispensed to the respective inmate;
caching electronic medical records for each inmate within the correctional facility unit scheduled to receive prescribed medication during the scheduled time period response to the step of scheduling; and
refusing to dispense prescribed medication to an inmate failing to match an identity of a scheduled inmate.

15. A method for computerized monitoring of dispensation of prescribed medication to prisoners in correctional facilities defining inmates in conjunction with computerized records including an electronic medical record, the electronic medical record containing information about an inmate to receive prescribed medication and the inmate's medical history, the method comprising the steps of:
performing an automated verification that an inmate is the inmate who has been prescribed the inmate's prescribed medication by a correctional facility unit computer prior to forming a record of dispensing a unit packet of the inmate's prescribed medication to the inmate responsive to reading an identification card for the inmate performed with a card swipes;
dispensing a unit packet of prescribed medication to an inmate;
forming a record of dispensing the unit packet of the inmate's prescribed medication to the inmate in a memory of a computer configured to manipulate and store dispensation, receipt verification, and administration verification records, the dispensation record formed responsive to the dispensing of the unit packet to the inmate;
verifying receipt by the inmate of the unit packet of the inmate's prescribed medication;
forming a receipt verification record in the memory of the computer indicating verification that the inmate received the unit packet of the inmate's prescribed medication responsive to verifying receipt by the inmate;
performing one of the following administration verification steps:
forming an administration verification record in the memory of the computer indicating an actual physical verification by a human observer that the inmate consumed the unit packet of the inmate's prescribed medication responsive to verifying consumption by the inmate, and
forming the administration verification record in the memory of the computer indicating that the inmate did not consume the unit packet of prescribed medication when so occurring;
providing a verification report responsive to the administration verification record to evidence that the respective correctional facility unit housing the inmate at least attempted to provide medical services for the inmate;
receiving a data entry from a correctional facility pill window technician for the correctional facility unit indicating an allergic reaction to the inmate's prescribed medication; and
updating the inmate's electronic medical record over a communications network responsive to the step of receiving the data entry indicating an allergic reaction to the inmate's prescribed medication.

16. The method of claim 15,
wherein the step of dispensing a unit packet of prescription medication to an inmate dispensing a 30 day supply of unit packets for the prescription medication; and
wherein the method further comprises performing the following steps responsive to the failure of the inmate to consume at least one unit packet of the inmate's prescribed medication:
subsequently locating the at least one unit packet of the inmate's prescribed medication;
returning the at least one unit packet of the inmate's prescribed medication, when determined to be suitable for future use, to a central pharmacy for reclamation; and
adjusting the inventory of pharmaceuticals accordingly.

17. A program storage device readable by a machine, tangibly embodying a machine readable code of program instructions executable by the machine to perform method steps of monitoring pharmaceutical inventory and monitoring of dispensation of prescribed medication to prisoners in correctional facilities defining inmates in conjunction with an electronic medical record containing information about an inmate to receive the prescribed medication and the inmate's medical history, the method steps of the program instructions in the machine readable code in the program storage device comprising the steps of:
performing a reviewing of the electronic medical record to include:
performing an automated review of an inmate's prescription and the inmate's electronic medical record responsive to entry of the prescription into an associated prescription system, and
displaying the inmate's electronic medical record and prescription for manual on-screen comparison by a pharmacist;
receiving an authorization to release of a prescribed medication for the inmate from the pharmacist;

providing data to print a label for the inmate's prescribed medication to place upon a unit packet of the inmate's prescribed medication;

performing an automated verification that the inmate is the inmate who has been prescribed the inmate's prescribed medication prior to forming a record of dispensing the unit packet of the inmate's prescribed medication to the inmate responsive a reading of an identification card identifying the inmate with a card swiper, forming a dispensation record in computer memory of dispensing the unit packet of the inmate's prescribed medication to the inmate responsive to receiving an indication that the unit packet of the inmate's prescribed medication was dispensed;

forming a receipt verification record in the computer memory indicating verification that the inmate received the unit packet of the inmate's prescribed medication responsive to receiving an indication verifying that the unit packet of the inmate's prescribed medication was received by the inmate;

performing one of the following administration verification steps:

forming an administration verification record in the computer memory of indicating an actual physical verification that the inmate consumed the unit packet of the inmate's prescribed medication responsive to receiving an indication verifying that the unit packet of the inmate's prescribed medication was consumed by the inmate, and forming the administration verification record in the computer memory indicating that the inmate did not consume the unit packet of prescribed medication responsive to receiving an indication that the inmate's prescribed medication was not consumed by the inmate;

receiving a data entry from a correctional facility pill window technician for the respective correctional facility unit indicating an allergic reaction to the inmate's prescribed medication; and updating the inmate's electronic medical record responsive to the data entry indicating an allergic reaction to the inmate's prescribed medication.

18. The program storage device of claim 17, wherein the method steps of the program instructions in the machine readable code in the program storage device further include the steps of:

scheduling shipping of each of a plurality of unit packets for each of a plurality of different prescribed medications for each separate one of a plurality of inmates to the respective correctional facility unit containing the plurality of inmates; and performing an automated update of a pharmaceutical inventory record based upon receipt of the unit packets by the correctional facility unit.

19. The program storage device of claim 18, wherein the method steps of the program instructions in the machine readable code in the program storage device further include the step of:

sorting each unit packet of the plurality of unit packets for each separate one of a plurality of inmates in the correctional facility unit into a shipment in accordance with a shipping schedule for delivery of each unit packet to the correctional facility unit after prescribed medication has been labeled.

20. The program storage device of claim 18, wherein the method steps of the program instructions in the machine readable code in the program storage device further include the step of:

preventing a potential disruption of medication administration resulting from a breakdown in network communications between a computerized records computer storing the inmate's electronic medical record and the correctional facility unit computer located remotely therefrom by caching in memory of the correctional facility unit computer at least portions of the electronic medical record for each inmate scheduled to receive prescribed medicines.

21. The program storage device of claim 18, wherein the method steps of the program instructions in the machine readable code in the program storage device further include the step of:

preventing a potential disruption of medication delivery resulting from a breakdown in network communications between a pharmacy computer and a remote computerized records computer storing electronic medical records and located remotely therefrom by caching in memory of the pharmacy computer each electronic medical record for each inmate contained within each shipment scheduled to be shipped within a predefined time period prior to the step of reviewing the inmate's electronic medical record.

22. The program storage device of claim 18, wherein the method steps of the program instructions in the machine readable code in the program storage device further include the step of:

preventing a potential disruption of medication delivery resulting from a breakdown in network communications between a pharmacy computer and a remote computerized records computer storing electronic medical records and located remotely therefrom by caching in memory of the pharmacy computer data related to each label to be printed for each shipment scheduled to be shipped within a predefined time period prior to printing the label.

23. A computerized system for monitoring of pharmaceutical inventory and dispensation of medication to prisoners in correctional facilities defining inmates in conjunction with an electronic medical record stored in a computer having a computer memory, the electronic medication record containing information about an inmate to receive prescribed medication and the inmate's medical history, the system comprising:

a pharmacy database stored in the computer memory for maintaining records related to a pharmaceutical inventory for correctional facilities and for maintaining a drug formulary of approved medication;

a pharmacist review workstation configured to enable a pharmacist to simultaneously review the inmate's electronic medical record and an inmate's prescription in computer memory and upon review of the inmate's prescription, approve the prescription;

a pharmacist technician workstation positioned remote from a correctional facility housing the inmate, and configured to enable pharmacist technicians to print labels with the printer for application to the inmate's prescribed medication upon command prior to delivery to the correctional facility;

a medication dispensation workstation positioned at the correctional facility and configured to enable the prescribed medication to be dispensed to an inmate and to enable a medication compliance history to be recorded in computer memory, the recording of the inmate's compliance history to include:
  performing an automated verification that the inmate is the inmate who has been prescribed the inmate's prescribed medication prior to forming a record of dispensing a unit packet of the inmate's prescribed medication to the inmate responsive to a reading of an identification card for the inmate with a card swipes,
  forming a record of dispensing the inmate's prescribed medication to the inmate in computer memory responsive to a pharmacy technician indicating the dispensing of the inmate's prescribed medication to the inmate,
  forming a receipt verification record in computer memory indicating verification that the inmate received the inmate's prescribed medication responsive to a pharmacy technician verifying receipt by the inmate, and
  performing one of the following administration verification steps:
    forming an administration verification record in computer memory indicating an actual physical verification that the inmate consumed the inmate's prescribed medication responsive to the pharmacy technician verifying consumption by the inmate, and
    forming the administration verification record in computer memory indicating that the inmate did not consume the unit packet of prescribed medication when so occurring,
  receiving a data entry from a correctional facility pill window technician for the correctional facility unit indicating an allergic reaction to the inmate's prescribed medication, and
  initiating an update of the inmate's electronic medical record over a communications network responsive to the data entry indicating an allergic reaction to the inmate's prescribed medication; and
the communications network electronically interconnecting the electronic medical record database, the pharmacy database, the pharmacist review workstation, the pharmacist technician workstation, the medication dispensation workstation, a printer, and the computer memory storing the electronic medical records to communicate with each other.

24. A computerized system for monitoring dispensation of medication to prisoners in correctional facilities of a prison system defining inmates in conjunction with an electronic medical record containing information about an inmate to receive prescribed medication and the inmate's medical history, the system comprising:
  a medication dispensation workstation positioned at a correctional facility and configured to enable the inmate's prescribed medication to be dispensed to the inmate and to enable a medication compliance history to be recorded in computer memory, the recording of the inmate's compliance history, to include:
    performing an automated verification that the inmate is the inmate who has been prescribed the inmate's prescribed medication prior to forming a record of dispensing a unit packet of the inmate's prescribed medication to the inmate responsive to a card swiper reading of an identification card of the inmate,
    forming a record of dispensing the inmate's prescribed medication to the inmate in the computer memory responsive to a pharmacy technician indicating the dispensing of the inmate's prescribed medication to the inmate,
    forming a receipt verification record in the computer memory indicating verification that the inmate received the inmate's prescribed medication responsive to a pharmacy technician verifying receipt by the inmate,
    performing one of the following administration verification operations:
      forming an administration verification record in the computer memory indicating an actual physical verification by a human observer that the inmate consumed the inmate's prescribed medication responsive to the pharmacy technician verifying consumption by the inmate, and
      forming the administration verification record in the computer memory indicating that the inmate did not consume the unit packet of prescribed medication when so occurring,
    receiving a data entry from a correctional facility pill window technician for the respective correctional facility unit indicating an allergic reaction to the inmate's prescribed medication, and
    initiating an update of the inmate's electronic medical record over a communications network responsive to the data entry indicating an allergic reaction to the inmate's prescribed medication.

25. The computerized system for monitoring dispensation of medication according to claim 24, further comprising:
  a communications network to enable an electronic medical record computer and the medication dispensation workstation to communicate with each other;
  a pharmacy database for maintaining inmate electronic medical records and records related to a pharmaceutical inventory for the correctional facility and for maintaining a drug formulary of approved medication for the correctional facility; and wherein
  the medication dispensation workstation is further configured to display a medical compliance or medical administration record for the inmate.

\* \* \* \* \*